United States Patent
Griffin et al.

(12)

(10) Patent No.: US 6,514,754 B1
(45) Date of Patent: Feb. 4, 2003

(54) VIRAL NUCLEOTIDE SEQUENCES

(75) Inventors: Annette Mary Griffin; Louis Joseph Norman Ross; Simon David Scott; Matthew McKinley Binns, all of Huntingdon (GB)

(73) Assignee: Merial, Lyons (FR)

( * ) Notice: Subject to any disclaimer, the term of this patent is extended or adjusted under 35 U.S.C. 154(b) by 0 days.

(21) Appl. No.: 09/304,110

(22) Filed: May 4, 1999

Related U.S. Application Data

(62) Division of application No. 08/460,257, filed on Jun. 2, 1995, now Pat. No. 5,965,435, which is a division of application No. 08/125,039, filed on Sep. 22, 1993, now Pat. No. 5,906,821, which is a continuation of application No. 07/669,391, filed as application No. PCT/GB89/01075 on Sep. 13, 1989, now abandoned.

(30) Foreign Application Priority Data

Sep. 13, 1988 (GB) .............................................. 8821441

(51) Int. Cl.[7] .......................... C12N 15/38; C12N 15/45; C12N 15/863; C12N 15/869
(52) U.S. Cl. ................................ 435/320.1; 435/235.1; 536/23.72
(58) Field of Search ............................. 435/235.1, 320.1; 536/23.72

(56) References Cited

PUBLICATIONS

Buckmaster et al. (1988) Gene sequence and mapping data from Marek's Disease Virus and Herpesvirus of Turkeys: implication for herpesvirus classification. J. Gen. Virol. 69:2033–2042, Aug. 1988.*

* cited by examiner

*Primary Examiner*—Robert A. Schwartzman
(74) *Attorney, Agent, or Firm*—Larson & Taylor PLC

(57) ABSTRACT

Various genes of herpes virus of turkeys (HVT), Marek's disease virus (MDV) and infectious laryngotracheitis virus (ILTV) have been identified as non-essential regions (and candidates for insertion sites for foreign genes) and/or as antigen-encoding regions. The former include the HVT homologue of the HSV (herpes simplex virus) gC gene, the TK (thymidine kinase) region of MDV or ILTV, ORF3 of ILTV (as defined herein), the ribonucleotide reductase (large subunit) gene of ILTV, MDV or HVT and the ribonucleotide reductase (small subunit) gene of MDV. The antigen-encoding regions include the HVT homologues of the HSV gB, gC and gH genes, the ILTV homologue of HSV gB, ORF2 of ILTV, and the HVT homologue of the HSV-1 immediate early genes IE-175 and IE-68. Manipulation of these genes allows vaccines to be prepared comprising attenuated virus or virus carrying heterologous antigen-encoding sequences.

6 Claims, 67 Drawing Sheets

```
TCGAGCTCGCCGGGGATGTTTAGTCACGATAGACATCGGT
         10        20        30        40

TCGCCCAGCCCGTCGAATACAGCATTATATTTTAGTGTTG
         50        60        70        80

AAAATGTAGGGCTGCTTCCTCACTTAAAGGAGAAATGGCT
         90       100       110       120

CGATTCATGTTTCATAGCAGTAGAAAAACAGATTGGACCG
        130       140       150       160

TCAGTAAGTTTAGAGGGTTTATGACTTTAGCACTATAGA
        170       180       190       200

TAATGTAACTGCGGCCCATCGGCTTGGAAATATATC
        210       220       230       240

AAAGAACTGATTTTTGCAACAGCTTTATTTTCTTCTGTAT
        250       260       270       280

TTAAAATGTGGCGAATTGCACATCTGTCGTGCCGACAGTTT
        290       300       310       320

GCAGATCAACAGCAATGGAGACTATGTATGGAAAAATGGA
        330       340       350       360
```

*FIG. 2A*

```
ATATATATAACATATGAAAACCGAATATCCACTTATAATGA
     370       380       390        400
TTCTGGGGTCAGAATCAAGCACTTCAGAAACGCAAAATAT
     410       420       430        440
GACTGCAATTATTGATACAGATGTTTTTTCGTTGCTTTTAT
     450       460       470        480
TCTATTTTTGCAGTATATGGCCCCCGTTACGGCAGATCAGG
     490       500       510        520
TGCGAGTAGAACAGATTACCAACAGCCACGCCCCCATCTG
     530       540       550        560
ACCCGTCCAATATTCTTGTGTCCCTGCATTTTATCTCACA
     570       580       590        600
                                      M  H
CAATTTATGAACAGCATCATTAAGATCATCTCACTATGCA
     610       620       630        640
 Y  F  R  R  N  C  I  F  F  L  I  V  I
CTATTTTTAGGCGGAATTGCATTTTTTTCCTTATAGTTATT
     650       660       670        680
```

FIG. 2B

```
L  Y  G  T  N  S  S  P  S  T  Q  N  V  T
CTATATGGTACGAACTCATCTCCGAGTACCCAAAATGTGA
        690           700          710          720

S  R  E  V  V  S  S  V  Q  L  S  E  E
CATCAAGAGAAGTTGTTTCGAGCGTCCAGTTGTCTGAGGA
        730           740          750          760

E  S  T  F  Y  L  C  P  P  P  V  G  S
AGAGTCTACGTTTTATCTTTGTCCCCCACCAGTGGGTTCA
        770           780          790          800

T  V  I  R  L  E  P  P  R  K  C  P  E  P
ACCGTGATCCGTCTAGAACCCGGCGAAAATGTCCCGAAC
        810           820          830          840

R  K  A  T  E  W  G  E  G  I  A  I  L
CTAGAAAAGCCACCGAGTGGGGGTGAAGGAATCGCGATATTA
        850           860          870          880
```

*FIG. 2C*

```
      F   K   E   N   I   S   P   Y   K   F   K   V   T
    TTTAAAGAGAATATCAGTCCATATAAATTTAAAGTGACGC
    |||||||||||||||||||||||||||||||||||||||
    GAGAATATCAGTCCGTATAAATTCAAAGTAACAC
              890        900         910        920

L   Y   Y   K   N   I   I   Q   T   T   T   W   T   G
    TTTATTATATAAAAATATCATTCAGACGACGACATGGACGG
    |||||||||||||||||||||||||||||||||||||||||
    TTTACTATAAGAACGTTATACAAACTACGACGTGGACTG
              930        940         950        960

T   T   Y   R   Q   I   T   N   R   Y   T   D   R
            GGACGACATATAGACAGATCACTAATCGATATACAGATAG
            |||||||||||||||||||||||||||||||||||||||
            GGACGACGTACAGACAGATAACTAACAGGTATACAGATAG
                970        980         990        1000
```

*FIG. 2D*

```
         ---D---                                              ---K---
    T  P  V  S  I  E  E  I  T  D  L  I  D        G  K  G  R  C  S  S  K  A  R  Y  L  R  N
GACGGCCCGTTTCCATTGAAGAGATCACGGATCTAATCGAC    GGCAAAGGAAGATGCTCATCTAAAGCAAGATACCTTAGAA
||||||||||||||||||||||||||||||||||||||||    ||||||||||||||||||||||||||||||||||||||||
AACACCCGTGTCTATCGACGAAATTACTGATTTGATAGAT    GGTAAGGGGAAATGTTCATCCAAAGCCCGGTATCTTCG
   1010        1020       1030       1040       1050       1060       1070       1080

N  V  Y  V  E  A  F  D  R  D  A  G  E        K  Q  V  L  L  K  P  S  K  F  N  T  P
ACAATGTATATGTGTTGAAGCGTTTGACAGGGATGCGGGAGAA    AAACAAGTACTTCTAAAACCATCAAAATTCAACACGCCCC
||||||||||||||||||||||||||||||||||||||||
   1090       1100       1110       1120       1130       1140       1150       1160
```

*FIG. 2E*

```
                    E   S   R   A   W   H   T   T   N   E   T   Y   T   V
                  GAATCTAGGGGCATGGCACACGACTAATGAGACGTATACCG
                                                           GGCATGGCATACGACCAACGAGACGTACACCG
                       1170        1180        1190        1200

—V—
                    W   G   S   P   W   I   Y   R   T   G   T   S   V
                  TGTGGGGATCACCATGGATATATCGAACGGGAACCCTCCGT
                  TGTGGGGATCTCCCATGGTATATAGAACGGGCACGTCCGT
                       1210        1220        1230        1240

—A—
                    N   C   I   V   E   E   M   D   A   R   S   V   F
                  CAATTGTATAGTAGAGGAAATGGATGCCCGCTCTGTGTTT
                  CAACTGCATAGTAGAAGAGATGGATGCCAGATCAGCATTT
                       1250        1260        1270        1280
```

*FIG. 2F*

```
         ----T-----------------------------
         P  Y  S  Y  F  A  M  A  N  G  D  I  A  N
         CCGTATTCATATTTGCAATGGCCAATGGCGACATCGCGA
         ||| || ||||||| ||||||||||||| || |||| |
         CCATACACGTACTTTGCAATGGCCAATGGAGATATCGCAA
              1290       1300      1310      1320

---M-----------T---T----T--D---------
         I  S  P  F  Y  G  L  S  P  P  E  A  A
         ACATATCTCCATTTTATGGTCTCTATCCCCACCAGAGGCTGC
         |||| ||||||||||||| || ||  ||||||||| ||||
         ACATGTCTCCATTTTATGGAACAACTCCAACCGACGCGGC
              1330      1340      1350      1360

------------S---------R----R-----
         A  E  P  M  G  Y  P  Q  D  N  F  K  Q
         CGCAGAACCCATGGGATATCCCCAGGATAATTTCAAACAA
         || ||| ||||| |||||||||||||||| ||||| |||
         CGCGGAGCCCATGAGCTATCCGCAAGACCGATTCAGGCAA
              1370      1380      1390      1400
```

*FIG. 2G*

```
          -F-------------------------P----------------------T---
            L   D   S   Y   F   S   M   D   L   D   K   R   R   K
          CTAGATAGCTATTTTCAATGGATTTGGACAAGCGTCGAA
             | |||||||||||| |||||||| ||||||||||||
          TTTGACAGCTATTTCCCCATGGATTTGGATACGGCCGAA
                        1410        1420        1430        1440

A   S   L   P   V   K   R   N   F   L   I   T   S
          AAGCAAGCCTTCCAGTCAAGCGTAACTTTCTCATCACATC
             ||
          AA
                  1450        1460        1470        1480

H   F   T   V   G   W   D   W   A   P   K   T   T
          ACACTTCACAGTTGGGGTGGGACTGGGCTCCAAAAACTACT
                  1490        1500        1510        1520

R   V   C   S   M   T   K   W   K   E   V   T   E   M
          CGTGTATGTTCAATGACTAAGTGGAAAGAGGTGACTGAAA
                  1530        1540        1550        1560

L   R   A   T   V   N   G   R   Y   R   F   M   A
          TGTTGCGTGCAACAGTTAATGGGAGATACAGATTTATGGC
                  1570        1580        1590        1600
```

*FIG. 2H*

```
R  E  L  S  A  T  F  I  S  N  T  T  E
CCGTGAACTTCGGCAACGTTTATCAGTAATACGACTGAG
     1610       1620       1630       1640

F  D  P  N  R  I  I  L  G  Q  C  I  K  R
TTTGATCCAAATCGCATCATATTAGGACAATGTATTAAAC
     1650       1660       1670       1680

E  A  E  A  A  I  E  Q  I  F  R  T  K
GCGAGGCAGAAGCAGCAATCGAGCAGATATTTAGGACAAA
     1690       1700       1710       1720

Y  N  D  S  H  V  K  V  G  H  V  Q  Y
ATATAATGACAGTCACGTCAAGGTTGGACATGTACAATA
     1730       1740       1750       1760

F  L  A  L  G  G  F  I  V  A  Y  Q  P  V
TTTCTTGGCTCTCTCGGGGGATTTATTGTAGCATATCAGCCCTG
     1770       1780       1790       1800

L  S  K  S  L  A  H  M  Y  L  R  E  L
TTCTATCCAAATCCCCTGGCTCATATGTACCTCAGAGAATT
     1810       1820       1830       1840
```

FIG. 21

```
  M  R  D  N  R  T  D  E  M  L  D  L  V
GATGAGAGACAACAGGACCGATGAGATGCTCGACCTGGTA
         1850      1860      1870      1880

N  N  K  H  A  I  Y  K  K  N  A  T  S  L
AACAATAAGCATGCAATTTATAAGAAAAATGCTACCTCAT
         1890      1900      1910      1920

S  R  L  R  R  D  I  R  N  A  P  N  R
TGTCACGCGATTGCGGGCGAGATATTCGAAATGCACCAAATAG
         1930      1940      1950      1960

K  I  T  L  D  D  T  T  A  I  K  S  T
AAAAATAACATTAGACGACACCACAGCTATTAAATCGACA
         1970      1980      1990      2000

S  S  V  Q  F  A  M  L  Q  F  L  Y  D  H
TCGTCTGTTCAATTCGCCATGCTCCAATTTCTTTATGATC
         2010      2020      2030      2040

I  Q  T  H  I  N  D  M  F  S  R  I  A
ATATACAAACCCATATTAATGATATGTTTAGTAGGATTGC
         2050      2060      2070      2080
```

FIG. 2J

```
       T  A  W  C  E  L  Q  N  R  E  L  V  L
       CACAGCTTGGTGTGCCGAATTGCAGAATAGAGAACTTGTTTTA
             2090        2100        2110        2120

W  H  E  G  I  K  I  N  P  S  A  T  A  S
       TGGCACGAAGGGATAAAGATTAATCCTAGCGCTACAGCGA
             2130        2140        2150        2160

|----
                                              A  K  M  L  G
                                              GCTGCAAAGATGTTGGG
                                              || || |||||||
                                              GCCAAAATGTTGGG
                                                      2190        2200
       A  T  L  G  R  R  V  A
       GTGCAACATTAGGAAGGAGAGTGGCT
             2170        2180

-----D----------------------I--E--T-----S-
D  V  A  A  V  S  S  C  T  A  I  D  A
GGATGTCGCTGCTGTATCGAGCTGCACTGCTATAGATGCG
 ||  || ||||||| ||||| |||   ||| |||
TGACGATGCCGCCCGTATCATCATGTATTGAGACTGATTCA
      2210        2220        2230        2240
```

FIG. 2K

```
         -D-------------------------------------------V---
          E   S   V   T   L   Q   N   S   M   R   V   I   T   S
         GAATCCGTCACTTTGCAAAATTCTATGCGAGTTATCACAT
         ||||||||||||||||||||||||||||||||||||||||
         GATTCTGTGTTACCTTACAAAATTCCATGCGGGTTGTCACCT
                 2250        2260        2270      2280

T   N   T   C   Y   S   R   P   L   V   L   F   S
         CCACTAATACATGTTATAGCCGACCATTGGTTCTATTTTC
         ||| ||||| ||||||||||||||||||||||||||||||
         CTACCAATACTTGTTATAGCCGCCCTTTAGTGTTATTCTC
            2290        2300        2310        2320

-----D--R-----D--K-----------------------------
          Y   G   E   N   Q   G   N   I   Q   G   Q   L   G
         ATATGGAGAAAACCAAGGAAACATACAGGGAACAACTCGGTG
         ||| |||||||||||||||| ||||||||||| |||| |||
         CTACGGGGACCGACAAGACACAAAATACAAGGACAGTTGGGGG
               2330        2340        2350      2360
```

FIG. 2L

```
                  I                                             I
  E   N   N   E   L  L  P   T  L   E   A   V  E   P
AAAACAACGAGTTGCTTCCAACGCTAGAGGCTGTAGAGC
||||||||||  ||  ||||||||  ||||||||||||||||||
AAAACAATGAATTGATTCCAACTCTAGAGGCCATAGAGC
         2370         2380         2390         2400

C   S   A   N   H   R   R   Y   F   L   F   G   S
CATGCTCGGCTAATCATCGTAGATATTTCTGTTTGGATC
|||  ||||||  ||||||||||||||  |
CATGTTCGGCCAATCATCGTAGA
         2410         2420         2430         2440

G   Y   A   L   F   E   N   Y   N   F   V   K   M
CGGTTATGCTTTATTTGAAAACTATAATTTTGTTAAGATGG
         2450         2460         2470         2480

V   D   A   A   D   I   Q   I   A   S   T   F   V   E
TAGACGCTGCCGATATACAGATTGCTAGCACATTTGTCG
         2490         2500         2510         2520
```

FIG. 2M

```
   L  N  L  T  L  L  E  D  R  E  I  L  P
AGCTTAATCTAACCCTGCTAGAAGATCGGGAAATTTTGCC
            2530      2540      2550      2560

L  S  V  Y  T  K  E  E  L  R  D  V  G
TTTATCCGTTTACACAAAAGAAGAGTTGCGTGATGTTGGT
            2570      2580      2590      2600

V  L  D  Y  A  E  V  A  R  R  N  Q  L  H
GTATTGGATTATGCAGAAGTAGCTCGCCGCAATCAACTAC
            2610      2620      2630      2640

E  L  K  F  Y  D  I  N  K  V  I  E  V
ATGAACTTAAATTTTATGACATAAACAAAGTAATAGAAGT
            2650      2660      2670      2680

D  T  N  Y  A  F  M  N  G  L  A  E  L
GGATACAAATTACGCGTTTATGAACGGTTTGGCCGAATTG
            2690      2700      2710      2720

F  N  G  M  G  Q  V  G  Q  A  I  G  K  V
TTTAACGGTATGGGTCAGGTAGGGCAAGCTATAGGCAAAG
            2730      2740      2750      2760
```

FIG. 2N

```
              V  V  G  A  A  G  A  I  V  S  T  I  S
TTGTAGTAGGGGCTGCCGTGCAATCGTATCTACCATATC
       2770              2780              2790              2800

G  V  S  A  F  M  S  I  P  L  G  L  S
TGGTGTCTCTGCTTTCATGTCAATCCCCTTTGGGCTTTCG
       2810              2820              2830              2840

A  I  G  L  I  I  A  G  L  V  A  A  F
GCAATCGGTTTAATCATTATAGCAGGACTCGTGGCTGCAT
       2850              2860              2870              2880

L  A  Y  R  Y  V  N  K  L  K  S  N  P
TTTAGCATATCGTTATGTAAACAAGCTTAAAAGCAATCC
       2890              2900              2910              2920

M  K  A  L  Y  P  M  T  T  E  V  L  K
AATGAAAGCCCTTTATCCTATGACAACAGAAGTGCTTAAG
       2930              2940              2950              2960

A  Q  A  T  R  E  L  H  G  E  E  S  D  D
GCACAGGCAACGCGTGAGTTGCATGGCGAGGAATCAGATG
       2970              2980              2990              3000
```

FIG. 20

```
  L   E   R   T   S   I   D   E   R   K   L   E   E
ATTTGGAACGAACATCTATTGATGAAAGAAAATTAGAAGA
              3010        3020        3030        3040

A   R   E   M   I   K   Y   M   A   L   V   S   A
AGCTAGAGAAATGATAAAATATGGCGTTAGTCTCCCGCG
        3050        3060        3070        3080

E   E   R   H   E   K   K   L   R   R   K   R   R   G
GAAGAACGCCACGAGAAAAACTGCGGAGAAAGAGGCGAG
        3090        3100        3110        3120

T   T   A   V   L   S   D   H   L   A   K   M   R
GCACTACCGCCGTTCTATCGGACCACCTGGCAAAATGAG
        3130        3140        3150        3160

I   K   N   S   N   P   K   Y   D   K   L   P   T
GATTAAAAATAGTAACCCTAAATATGATAAGTTACCTACT
        3170        3180        3190        3200

T   Y   S   D   S   E   D   D   A   V   *
ACATATTCAGACTCAGAAGATGATGCTGTGTAAGTGGGCA
        3210        3220        3230        3240

CTATTTATATTTGAACTGAATAAAAACGCATAGAGCATGATA
        3250        3260        3270        3280
```

FIG. 2P

```
TGGTTTACTCATTTATTGCGAGAGATATAAAGCATATTCAAT
3290      3300      3310      3320

ACGATATATTGCGAACGTGATGCTAAAAACATAGCTCCCT
3330      3340      3350      3360

GTATTATTGATGCGCCATCATTTGATTAATAAATACATCG
3370      3380      3390      3400

ACGCCGGCATCACTGGTGCGGGTGTATACCAGCTACGGCGC
3410      3420      3430      3440

TAGCATTCATGGTATCCCCGTGATTGCTCGATGCTTTCCTT
3450      3460      3470      3480

CTGAATTCCGTCGGAACGCTCCTGAGAGATGGTCGCAGTT
3490      3500      3510      3520

ATTGGTACATTTCGACCAGCCTCCGGATCTGAAACTGGCA
3530      3540      3550      3560

CAGGAATGCACCGTGGAATTGGTAGAAGTTTTTCCTTCCG
3570      3580      3590      3600
```

*FIG. 2Q*

TGGAAGGCATAGGGCGTTCGACTCCCATGGGCCATGAAACTGTGTGGATGT
   3610          3620          3630          3640          3650

FIG. 2R

```
TATTATTGGTCCATGCTAGAATAGTCATACGCTACGATCT
         10        20        30        40

GTTGCTATATATGACTATCGCCAAACTGTTAAACCCGCGA
         50        60        70        80

AGAATATATTTCATATAAACCTAAGGGCCCCCTCAGTCTGA
         90       100       110       120

M   K   F   Y   C   L
TTTTTTGTGAAAAACGTGTATACCATGAAGTTTTACTGCCT
        130       140       150       160

I   R   F   M   I   I   A   N   L   Y   S   S   Y
AATCCGTTTCATGATCATAGCGAATCTTTATTCATCTTAC
        170       180       190       200

Q   I   S   L   P   G   T   Y   P   S   Q   I   L   L
CAAATATATCGCTTCCAGGCACATATCCATCGCAAATATTGC
        210       220       230       240

D   M   K   N   S   P   L   V   R   F   N   I   S
TTGACATGAAGAACTCGCCGCTACGCTTCGTGTTTAATATATC
        250       260       270       280
```

FIG. 4A

```
         T  R  D  Y  K  D  E  T  L  W  I  R  K
         GACGCGGTGATTATAAAGACGAGACACTCTGGATACGGAAA
               290         300         310         320

N  S  T  F  V  Y  I  D  T  A  V  T  T  A
         AATTCGACATTTGTTTATATCGATACGGCTGTGACGACAG
               330         340         350         360

N  V  I  F  Y  L  P  I  G  Q  V  R  Q
         CGAACGTTATCTTTTATCTGCCGATCGGTCAGGTACGACA
               370         380         390         400

M  V  F  F  K  R  P  I  S  R  L  L  T
         AATGGTTTTTTTCAAGCCGTCCAATATCCAGGCTACTAACG
               410         420         430         440

S  N  N  L  V  K  F  I  N  T  G  S  Y  A
         TCCAATAACCTGGTTAAATTTATTAATACCGGTTCATACG
               450         460         470         480

N  H  T  F  K  T  E  L  S  P  Y  L  S
         CCAATCATACATTCAAGACAGAACTTTCACCCTATTTGTC
               490         500         510         520
```

*FIG. 4B*

```
K  T  N  T  P  L  K  K  Y  E  I  V  V
GAAAACCAATATACACCGTTGAAGAAATATGAAATTGTTGTC
         530           540          550           560

D  Q  P  T  G  E  N  P  P  A  G  F  G  S
GATCAACCTACTGGAGAAAACCCCTCCGGCAGGGTTCGGAA
         570           580          590           600

L  K  P  A  D  F  L  N  P  G  Y  K  F
GTTTAAAACCGGCAGACTTTCTCAACCCCGGATACAAGTT
         610           620          630           640

V  L  T  S  E  L  V  G  A  Y  T  K  R
CGTTCTCACAAGCGAGTTGGTAGGAGCCTACACAAAACGA
         650           660          670           680

S  C  F  V  D  P  M  D  S  L  V  P  I  D
TCTTGTTTTGTCGATCCGATGGATTCTCTCGTCCCGATAG
         690           700          710           720

Y  D  H  V  R  T  I  I  F  G  S  A  G
ATTATGATCATGTACGAACCATTATATTCGGATCTGCTGG
         730           740          750           760
```

```
         M  E  I  L  M  K  M  G  I  T  L  A  S
        GATGGAGATTTTAATGAAGATGGGAATTACTTTGGCATCT
              770       780       790       800

M  T  I  S  T  K  Y  N  P  P  I  E  L  I
ATGACCATTTCGACGAAATATAATCCTCCTATTGAACTGA
      810       820       830       840

I  S  A  K  Y  R  N  L  S  L  L  W  P
TAATATCTGCAAAGTACCGAAATTTATCACTGTTGTGGCC
      850       860       870       880

P  R  Q  Q  Y  E  P  V  N  K  G  T  G
ACCCCGACAACAATATGAACCTGTAAATAAAGGGACTGGA
      890       900       910       920

R  P  H  W  I  Y  L  L  G  V  Y  R  N  V
CGCCCCCATTGGATCTACCTATTAGGTGTGTATAGAAACG
      930       940       950       960

S  D  S  E  R  D  S  Y  M  N  M  I  K
TTTCGGACTCCGAGCGTGACTCATACATGAATATGATTAA
      970       980       990       1000
```

```
  S   L   G   D   S   M   D   Y   H   F   L   I   S
GAGTCTGGGGCGATTCTATGGATTATCACTTCCTAATTAGC
         1010         1020         1030         1040

R   A   H   A   Q   M   L   I   L   A   A   E   D   R
AGAGCGCATGCCCAGATGCTGATACTGGCCAGCAGAGGACC
         1050         1060         1070         1080

L   V   D   E   M   H   S   F   R   N   V   I   A
GGCTCGTGGATGAAATGCATAGTTTCAGGAACGTTATTGC
         1090         1100         1110         1120

R   L   F   V   S   L   F   A   F   I   R   N   A
GCGTTTATTTGTATCGTTGTTCGCATTCATACGTAACGCA
         1130         1140         1150         1160

F   Q   S   G   Y   T   S   L   N   D   I   E   I
TTTCAGTCTGGCTACACCTCTCTTAATGACATAATTGAAA
         1170         1180         1190         1200

E   A   D   L   R   L   I   V   E   G   I   S   S
TCGAAGCCGATTTGAGGTTAATTGTAGAAGGCATTTCTTC
         1210         1220         1230         1240
```

FIG. 4E

```
  A   A   F   R   K   D   A   S       T   H   F   L   I
TGCTGCATTTCGTAAAGACGCTAGTACACACTTTCTTATA
        1250            1260            1270            1280

S   G   T   P   I   K   D   S   K   A   D   L   I   K
TCGGGAACGCCCATAAAAGATAGCAAAGCGGATTAATTA
        1290            1300            1310            1320

S   L   L   S   K   V   I   R   P   I   S   G   H
AATCGTTGTTGTCTAAAGTCATTCGACCAATTTCCGGACA
        1330            1340            1350            1360

T   R   P   L   S   A   I   Q   H   L   F   L   L
TACACGTCCCTTATCTGCGATACAACATCTATTCCTTTTG
        1370            1380            1390            1400

R   S   A   Y   A   L   D   I   P   R   Q   N   G   S
AGATCCGCTTATGCATTGGATATACCCCGTCAAAACGGAT
        1410            1420            1430            1440

L   S   E   Q   V   S   T   V   A   L   S   F   I
CTTTGAGCAACAGGTATCTACAGTGGCACTGTCGTTCAT
        1450            1460            1470            1480
```

FIG. 4F

```
E  N  I  H  S  E  A  M  R  D  I  L  S
TGAAAATATTCACAGCGAGGCCATGAGGGACATTCTGTCA
     1490      1500      1510      1520

W  N  T  T  K  H  A  L  Y  Y  A  F  A
TGGAACACTACAACAAAGCATGCCGTTGTATTATGCATTCG
     1530      1540      1550      1560

S  I  L  Q  R  P  L  T  E  W  G  A  S
CGAGTATTTTGCAACGGCCACTGACCGAATGGGGCCCTC
     1570      1580      1590      1600

R  N  A  R  R  A  I  L  L  A  S  S  M
AAGAAATGCACGGAGGCAATACTATTAGCATCATCGATG
     1610      1620      1630      1640

C  T  E  E  H  V  I  A  T  E  L  A  I  Q
TGTACAGAAGAGCATGTTATCGCAACTGAGTTGGCTATTC
     1650      1660      1670      1680

E  L  Y  V  K  I  R  S  N  A  D  P  I
AAGAACTGTATGTCAAAATCAGAAGTAATGCCGACCCAAT
     1690      1700      1710      1720
```

FIG. 4G

```
  H   L   D   V   Y   T   P   C   L   S   S   L
ACACCTTCTAGACGTATATACACCATGTCTTTCTTCACTA
         1730          1740          1750          1760

R   L   D   L   S   E   H   H   R   I   Y   A   M   A
CGATTGGACCTTTCCGAACACCATCGGATATACGCAATGG
         1770          1780          1790          1800

D   V   V   F   Y   P   D   I   Q   Q   Y   L   K
CAGATGTAGTTTTCTATCCAGACATTCAGCAGTATTTGAA
         1810          1820          1830          1840

K   K   S   H   E   G   N   M   K   E   D   D   L
AAAAAATCCCATGAGGGTAATATGAAGGAAGATGATCTC
         1850          1860          1870          1880

E   T   K   A   E   Y   I   L   T   K   L
GAAACAAAGGCGGAATACATCCTCACCAAGCTT
         1890          1900          1910
```

FIG. 4H

```
AAGCTTTTTGTAAAAACGATTATGACCACGGACACCCGCT
         10        20        30        40

TTTAGCAATCCTGCCATAAGGTGGTTTCCCGCGTGCTTGC
         50        60        70        80

CTCGAAGACAATTGCCAGCTAATCCCAGCATTACCATATTT
         90       100       110       120

----S--Q
                                    M  A  L  P
CCTTGGCTTGCATTTGGATCTGCCGTCGATGGCATTGCC
                                    ||||||||
                                    ATGGCATCTCA
        130       140       150       160

--M--T--S--A--Q-----I-----------------
  R  R  P  P  T  L  T  R  V  Y  L  D  G
GAGAAGACCGGCCCCACGTTAACGCGAGTTTATCTAGACGGA
||||||||||||||||||||||||||||||||||||||||
GATGACATCTGCACAGCTCATACGTGTATACCTCGATGGA
        170       180       190       200
```

*FIG. 5A*

```
       -S---M-------------M------E---I--
        P  F  G  I  G  K  T  S  I  L  N  A  M  P
       CCGTTTGGTATAGGCAAAACGTCTATACTAAACGCTATGC
        |  |  ||||||||||||||||  ||||||| ||||| |
       TCAATGGGTATAGGTAAAACGTCAATGTTGAATGAGATAC
              210         220         230         240

---T-----L|
        D  H  T  P  D  G  A  P  I  L  K  V  Y
       CCGACCACACGCCCGATGGGGCTCCTATATTGAAAGTGTA
        ||
       CGACATCTT
              250         260         270         280

E  P  M  K  Y  W  R  C  Q  S  T  D  L
       CGAACCAATGAAATATTGGAGATGCCAGTCTACCGATTTG
              290         300         310         320
```

FIG. 5B

```
      ---------R---
V  V  A  A  N  E  T  P  E  R  R  R  G  G
GTGGTAGCTGCCAACGAAACGCCAGAACGTAGGCGTGGTG
                                       ---
                       ATCGTCGTCGCAGGG
           330            340            350           360

---E---F---L-------         ---S-------V--T--A
 A  L  S  G  F  Q  S  D  M  I  M  A  S
GAGCTTTATCACGATTCCAATCTGACATGATCATGGCATC
||||||| ||||| |||||||||||||||||| |||||||
GAGAGTTTTCTTTATTTCAATCTAGCATGATTGTAACAGC
           370            380            390           400

---L-----S--K-------         ---------V-----------
 I  Q  A  R  F  A  D  P  Y  L  L  F  H
TATACAAGCCCAGATTTGCCGATCCATATTGCTTTTTCAC
||| |||| |||||| |||||||||||| ||||||| |||
TTTACAATCAAAAGTTTGCAGATCCCTATCTTGTATTTCAT
           410            420            430           440
```

*FIG. 5C*

```
         H--R--I--T--G--T--R
E  R  L  S  S  K  C  R  G  K  I  E  I  C
GAACGGTTATCATCTAAATGTAGAGGAAAAATAGAAATAT
|  |  |  |  |  |  |  |  |  |  |  |  |  |
GAGCGGCTTATCGTCGAAGTGTCATCGCATAACAGGAACAC
        450         460         470         480

G--N-----S--L-----I
D  T  P  A  I  I  L  M  L  D  R  H  P
GCGATACTCCAGCAATTATATTAATGCTGGATAGGCACCC
|  |  |  |  |  |  |  |  |  |  |  |  |
GTGGCAATCCATGCTTATATTAATTCTAGATCGACATCC
        490         500         510         520

I--S-----T--V-----------A-----H
V  A  A  I  L  C  F  P  I  T  R  Y  L
TGTGGCGGCGATATTATGTTTCCCAATCACTCGCTATTTA
|  |  |  |  |  |  |  |  |  |  |  |  |
CATATCCGCTACCGTATGTTTTCCCATTGCTCGACATTTA
        530         540         550         560
```

*FIG. 5D*

```
-T----D---C---------------------------------M----------------
 L   G   E   Y   S   L   E   M   L   I   S   S   I   I
CTTGGAGAATATTCTTTGGAAATGTTGATTAGCTCTATAA
||| |||||||  |||| ||||||| ||||||| ||||||
ACTGGAGATTGTTCCTTGGAGATGCTAATTAGTATGATAA
        570         580         590         600

-------------Q-------P-------------V--I----------------------
 R   L   P   L   E   S   P   G   C   N   L   T   V
TAAGACTTCCGTTGGAATCCCCCGGATGCAACCTGACAGT
|| |||||||| |||| ||  ||||||||||| |||| ||
TAAGGTTGCCCCCAGGAACCGCCAGGATGCAACTTGGTGAT
        610         620         630         640

--V--D-----H-----------------------------S-----L-----
 T   I   L   P   D   E   K   E   H   V   N   R   I
CACAATCCTTCCCGACGAAAAGGAACACGTTAATAGGATT
|| ||||| || |||||||||||| |||||| ||  ||
TGTCGATCTACATGACGAAAAGGAGCATGTTAGCCGTCTA
        650         660         670         680
```

*FIG. 5E*

```
    S-----N-----T-----T-----L-----L---
    C  S  R  D  R  P  G  E  T  A  D  R  N  M
    TGTTCAAGAGATAGACCGGGTGAAACGGCAGATAGAAATA
    ||| ||||| ||||| ||||||||||| ||||| |||||
    TCTTCACGGAATAGGACCGGGAGAAAACAGATCTACTAA
            690       700       710       720

----------A-----S-----C-----L-----V---D
    L  R  T  L  N  A  V  Y  A  S  L  V  D
    TGCTCAGAACACTCAATGCCGTATACGCATCTTTGGTGGA
    ||||||| |||||||||||| || |||||||| |||  ||
    TGCTCAGGGCACTTAATGCAGTGTATTCCTGTTTAGTAGA
            730       740       750       760

-I---M---------H-----I---------S---
    T  V  K  Y  A  N  L  T  C  P  Y  E  K
    CACGGTTAAATACGCAAATCTAACATGCCCTTACGAGAAA
    || |||||||||||||| |||||||  ||||| |||||||
    CACTATTATGTACGCAAATCATATTTGTCCCTACAGTAAG
            770       780       790       800
```

*FIG. 5F*

```
 -D--E-------S-------D-------D
  E  S  W  E  M  E  W  L  G  L  P  W  F  E
GAAAGCTGGGAAATGGAAATGGAATGGTTGGGGACTTCCCTGGTTTG
|||  ||||||||  |||  ||||||  ||||||  ||| ||||||
GATGAATGGGAATCTGAATGGTTGGGGATCTACCATGGTTTG
     810            820           830           840

---T-----A--T---------N--E------T
  E  S  L  L  E  E  F  I  S  R  P  R  P
AAGAGTCATTACTTGAAGAATTCATCTCGCCCCCGCCC
    |||| ||   |||  |||||||  |||||
ATACATCTTTGGCCCAACGTTTATAAACGAACCTCGTAC
     850           860           870           880

--...D--Y--R--G--S----V--S---H--H----
  V  I  C  S  R  T  R  M  P  L  D  R  T
TGTTATTTGTTCGAGAACTCGAATGCCGCTGGACCGAACT
||    |||  ||  ||  |||  ||||||  |||||||
TG...ATTATCGCGGTAGTAGGGTGTCATTACACCATACG
     890           900           910           920
```

FIG. 5G

```
       |--------R-------|
    L  L  A  I  F  K  R  K  E  L  C  S  E  N
    CTCCTGGCCATTTTTAAACGGAAAGAGCTGTGTAGCGAAA
       |||||||  ||| |||  ||  |||||| |||
       CTTTTAGCGATATTTAAGCGGGCGAGAATTATGT
    930          940          950          960

G  E  L  L  T  Q  Y  S  W  I  L  W  G
    ATGGGGAGCTGTTAACTCAGTATTCTTGGATATTGTGGGG
    970          980          990          1000

L  T  K  L  H  T  I  N  V  E  L  F
    ATTACTGACTAAACTACACACCATTAATGTCGAATTATTT
    1010         1020         1030         1040

|---V--E--L--L
    D  I  S  G  M  S  R  R  E    C  A  S  A  I
    GACATTAGCGGGTATGTCAGAGAATGCGCCAGCGCTA
    1050         1060         1070
                                 TGTGTAGAACTGC
                                 1080
```

FIG. 5H

```
        ---D---      ---S---      ---V---H---S---
         M  H  T  M  P  E  R  L  S  T  L  A  S
       TAATGCATACTATGCCGGAGAGATTGTCTACTCTCGCTAG
       |||||||||| ||||||||||||||||||||||| |||||
       TTATGGATACTATGTCGGAGAGATTGGTAACACATAGTAG
        1090         1100         1110         1120

---A---F---I---A---      ---L---A-
         W  N  D  L  C  E  L  E  D  D  V  I  S
       CTGGAATGATTTATGCGAGCTTGAAGATGATGTAATTTCC
       ||||||||||| |||| |||||||||||||| |||| |||
       CTGGAATGATGATGCCTTCGAGATTGAAGCTGATGTACTAGCC
        1130         1140         1150         1160

---E---A---M---*|
         Y  N  K  G  M  C  N  E  V  G  A  S  R  *
       TATAATAAGGGAATGTGTAACGAGGTTGGAGCCGTCTCGAT
       ||||||||||||||||||    ||||
       TATAATAAAGAGAGATGGCTATGTAA
        1170         1180         1190         1200

AATTCTTCTTAATCTGCTGGTATTGGTTACTGCCATAACT
        1210         1220         1230         1240
```

*FIG. 5I*

TATTATTGGTCCATGCTAGAATAGTCATACGCTACGATCT
1250      1260      1270      1280

GTTGCTATATATGACTATCGCCAAACTGTTAAACCCGCGA
1290      1300      1310      1320

AGAATATATTTCATATAAAACCTAAGGGCCCCTCAGTCTGA
1330      1340      1350      1360

TTTTTTGTGAAAAACGTGTATACCA
1370      1380

```
  1 CAGCTGCCTATGTAGTGAAATCTATACTGGGATTT
    ATCATAAACTAGTTTACTTGTTTGTATATTAGTAGCCGCTATCT
    TGACCAAATCGTTGTTCACATCTTGGCCATATACGTATTGATC
121 GTTGTTTCGAACCGCGAATAAAACTTTCATACATAC
    TAAACGATGGAGTTGTGTTTATGAGCCGTTGAAAACAAAGGT
    ACCATCGGTTAAAACTAAGTTGCATATCGTAATCCACAAAA
241 ATCATTTTATACATCATCCCGAAGAGACACCAAACG
                        M  L  T  P  R  V
    TAACCCTCTACATATCTTCCCTCATGCTCACGCCGGTGTGT
                                      L  L  S
    TACGAGCTTGGGGTGGACTCTTTTTTTGCTTTTAT
    L  R  A  L  G  W  T  G  L  F  F  L
            P  S  N  V  L  G  A  S  L  S  R
361 CTCCGAGCAACGTCCTAGGAGCCAGCCCTTAGCCGG
    D  L  E  T  P  P  F  L  S  F  D  P  S
    GATCTCGAAACACCCCCATTTCTATCCCTTTGATCCATCCA
```

```
N  I  S  I  N  G  A  P  L  T  E  V  P  H  A  P
ACATTCAATTAACGGCGCCCTTTAACTGAGGTACCTCATGCAC
                                S  T  E  S  V  S  T  N  S  E  S  T
481 CTTCCACAGAAAGTGTCAACAAATTCGGAAAGTACC

N  E  H  T  I  T  E  T  T  G  K  N  A  Y
AATGAACATACCATAACAGAGAACGACGGGCAAGAACGCATACA

I  H  N  N  A  S  T  D  K  Q  N  A  N  D
TCCACAACAATGCGTCTACGGACAAGCAAAATGCCAACG
                                      T  H  K  T  P  N  I  L  C  D  T  E
601 ACACTCAAAACGCCCAATATACTCTGCGATACGGA

E  V  F  V  F  L  N  E  T  G  R  F  V  C
AGAAGTTTTTGTTTTCCTTAACGAACGGGAAGATTTGTTTGT

T  L  K  V  D  P  P  S  D  S  E  W  S  N
ACTCTCAAAGTCGACCCCCTCGGATAGTGAATGGTCCA
                                F  V  L  D  L  I  F  N  P  I  E  Y
721 ACTTTGTTCTAGATCTTGATCTTTAACCCAATTGAATA

H  A  N  E  K  N  V  E  A  R  I  A  G
CCACGCCAACGAAAAGAATGTGGAAGCGGCGTATCGCTGGT
```

FIG 6B

```
         L  Y  G  V  P  G  S  D  Y  A  Y  P  R  Q
     CTCTATGGAGTCCCCGGATCAGACTATGCATACCCACGTC

S  E  L  I  S  S  I  R  D  P
841  AATCTGAATTAATTTCTTCGATTCGACGAGATCCCC

Q  G  T  F  W  T  S  P  S  P  H  G  N  K
     AGGGCACACATTTTGGACGAGCCCCATCACCTCATGGAAACAA

Y  F  I  W  I  N  K  T  N  T  M  G  V  E
     GTACTTCATATGGATAAACAAACAATACGATGGGCGTGG

I  R  N  V  D  Y  A  D  N  G  Y
961  AAATTAGAAATGTAGATTATGCTGATAATGGCTAC

M  Q  V  I  M  R  D  H  F  N  R  P  L
     ATGCAAGTCATTATGCGTGACCATTTTAATCGGCCTTTAA

I  D  K  H  I  Y  I  R  V  C  Q  R  P  A  S  V
     TAGATAAACATATTTACATACGTGTGTCAACGACCTGCATCAG

D  V  L  A  P  P  V  L  S  G  E  N
1081 TGGATGTACTGGCCCCTCCAGTCCTCAGCGGAGAAAA

Y  K  A  S  C  I  V  R  H  F  Y  P  P  G
     TTACAAGGCATCTTGTATCGTTAGACACTTTTATCCCCTGGA
```

*FIG. 6C*

```
      S V Y V S W R Q N G N I A T
      TCTGTCTATGTATCTTGGAGACAGAATGGAAACATTGCAA

P R K D R D G S F W W F
1201 CTCCTCGGAAAGATCGCGATGGAAGTTTTTGGTGGTT

E S G R G A T L V S T I T L
      CGAATCTGGTAGAGGAGCTACGTTGGTTTCTACAATAACATTG

G N S G I D F P P K I S C L
      GGAAATTCAGGAATTGATTCCCCCCAAAATATCTTGTC

V A W K Q G D M I S T T
1321 TGGTTGCCTGGAAGCAGGGTGATATGATCAGCACGAC

N A T A I P T V Y H H P R L
      GAATGCCACAGCTATCCCGACGGTATATCATCATCCCCGTTTA

S L A F K D G Y A I C T I E
      TCCCTGGCTTTTAAAGATGGGTATGCAATATGTACTATAG

C V P S E I T V R W L V
1441 AATGTGTCCCCTCTGAGATTACTGTACGGTGGTTAGT

H D E A Q P N T T Y N T V V
      ACATGATGAAGGCCAGCCTAACACAACTTATAATACTGTGGTT
```

*FIG. 6D*

```
     T  G  L  C  R  T  I  D  R  H  R  N  L  L
     ACAGGTCTCTGCCGGACCATCGATCGGCCATAGAAATCTCC

S  R  I  P  V  W  D  N  W  T  K  T
1561 TCAGCCGCATTCCAGTATGGGACAATTGGACGAAAAC

K  Y  T  C  R  L  I  G  Y  P  F  D  E  D
     AAAATATACGTGCAGACTCATAGGCTACCCCTTCGATGAAGAT

K  F  Q  D  S  E  Y  Y  D  A  T  P  S  A
     AAATTCAAGATTCGGAATATTACGATGCAACTCCATCTG

R  G  T  P  M  V  I  T  V  T  A  V
1681 CAAGAGGAACACCCATGGTTATTACGGTTACGGCAGT

L  G  L  A  V  I  L  G  M  G  I  M  T
     TTTGGGATTGGCTGTAATTTTAGGGATGGGATAATCATGACT

A  L  C  L  Y  N  S  T  R  K  N  I  R  L
     GCCCTAGTGTTTATACAACTCCACACGAAAAAATATTCGAT

*
1801 TATAATCTCATTGTTATGTAGTTGTGATTTATTAAAC

ATATTTTTATAACTCTAGTATTCTCCGAGTACTTATATATT
```

FIG. 6E

TATTTGTCAGACAATAATGCAATAGTGGAGAAACGTGAGG
1921 GGAGTCTGTAAACAGAATACGTATAATCATCTATTTG
AATAAAAGATTGTGGTATAAATGAAGATAGCCGCAAGTCATTC
CAAGCTCTCCATTCTATTTAAACAATGTACAGTTTAAAGT

FIG. 6F

HVT HOMOLOGUES OF VZV62/ HSV-1 IE 175

```
 S  N  V  V  R  Y  M  C  G  N  T  V  L
TCGAATGTGGTGCGATACATGTGCGGGAACACGGTACTCC
        10        20        30        40

P  P  D  P  H  G  T  P  V  V  I  N  V  P
CCCCGGATCCCCATGGCACCCCCGTGGTGATCAACGTTCC
        50        60        70        80

E  G  T  S  E  T  M  A  E  L  T  V  A
CGAGGGAACGTCCGAAACTATGGCGGAGCTTACTGTTGCT
        90       100       110       120

H  V  G  R  K  S  I  G  W  P  T  S  E
CACGTTGGGCGCAAGTCTATTGGGTGGCCGACCTCCGAGT
       130       140       150       160

W  H  S  A  T  I  L  Q  K  D  N  D  S  R  L  V  I  I  R
GGCATTCCGCTACAATCCTGCAGAAAGATAATGATAGTCGGCTGGTAATTATACGCC
       170       180       190       200       210
```

FIG. 7

HVT HOMOLOGUE OF RIBONUCLEOTIDE
REDUCTASE (LARGE SUBUNIT)

```
Q   V   T   E   V   S   E   G   F   A   P   L   F
CAAGTGACCGAGGTTAGCCGAAGGATTTGCCCCTTTGTTCA
         10           20           30       40
S   N   M   F   S   K   V   T   S   A   G   E   L   L
GTAACATGTTCAGCAAGGTGACAAGTGCCGGGGAACTGCT
         50           60           70       80
R   P   N   S   Q   L   M   R   E   L   R   Q   I
TAGACCCAACAGTCAATTAATGCGGGAGCTGAGACAAATA
         90          100          110      120
Y   P   D   N
TATCCCGATAAT
   130
```

FIG. 8

MDV HOMOLOGUE OF RIBONUCLEOTIDE
REDUCTASE (LARGE SUB-UNIT)

```
       G   I   M   E   G   S   D   V   P   T   E   K   S
      GGGGATAATGGAAGGAAGTGATGTACCGACGGAAAAATCT
               10        20        30        40

H   S   G   R   E   R   N   R   S   M   G   I   G
  CATTCTGGCCGAGAACGTAACAGATCGATGGGCATCGGCG
           50        60        70        80

V   Q   G   F   H   T   A   F   L   S   M   G   L   D
  TGCAGGGCTTTCATACAGCTTTTCTATCTATGGGTCTTGA
           90       100       110       120

L   C   D   E   R   A   R   S   L   N   K   L   I
      TTTATGCGATGAACGCGGCTAGATCCCTCAACAAGCTAATT
               130       140       150       160

F   E   F   M   L   L   E   A   M   T   V   S   C
  TTTGAATTCATGTTATTGGAGGCGATGACAGTTAGTTGCG
          170       180       190       200

E   F   C   E   R   G   L   P   P   F   A   D   F   S
  AATTCTGCGAACGAGGCCTGCCGCCGTTTGCTGATTTCTC
          210       220       230       240
```

FIG. 9A

```
  N   S   Y   Y   A   R   G   R   L   H   F   D   G
TAACAGTTATTATGCACGGAGGACGTCTGCATTTCGATGGG
        250       260       270       280

W   A   N   V   E   L   A   A   V   E   E   W   N
TGGGCTAATGTAGAATTGGCTGCAGTGGAAGAGTGGAATA
        290       300       310       320
```

FIG. 9B

MDV HOMOLOGUE OF RIBONUCLEOTIDE
REDUCTASE (SMALL SUB-UNIT)

```
   L   D   V   E   A   I   L   C

MDV HOMOLOGUE OF HSV-1 IE-175

```
 P  I  P  V  Y  V  E  E  M  K  D  Y  A
 CCCATTCCCGTCTATGTAGAGGAAATGAAAGATTATGCCA
         10        20        30        40

K  Q  Y  D  A  L  V  N  S  L  F  H  K  S
AACAATACGACGCTCTCGTAAACTCTTTGTTTCACAAAAG
        50        60        70        80

M  K  V  N  P  L  N  W  M  H  H  G  K
CATGAAAGTAAATCCTCTGAACTGGATGCACCACGGGAAG
        90       100       110       120

L  S  T  A  D  A  A  L  N  H  I  Y  V
 CTGTCTACCGCCGATGCTGCCCTAAACCACATATATGTTC
        130       140       150       160

Q  K  F  Q  S  S  Y  D  S  P  G  A  A  V
AGAAATTCCAGAGTTCATACGATTCGCCCGGAGCGGCTGT
       170       180       190       200

T  G  T  V  N
AACTGGCACAGTTAACA
       210
```

*FIG. 11*

MDV HOMOLOGUE OF HSV-1 IE-68

```
          S   D   Q   D   F   E   L   N   N   V   G   K   F
          CGTCCGATCAAGAGACTTTGAACTTAATAATGTGGGCAAATT
                    10        20        30        40

C   P   L   P   W   K   P   D   V   A   R   L   C
  TTGTCCTCTACCATGGAAACCCGATGTCGCTCGGTTATGT
            50        60        70        80

A   D   T   N   K   L   F   R   C   F   I   R   C   R
  GCGGATACAAACAAACTATTTCGATGTTTTATTCGATGTC
            90       100       110       120

L   N   S   G   P   F   H   D   A   L   R   R   A
  GACTAAATAGCGGTCCGTTCCACGATGCTCTTCGGAGAGC
           130       140       150       160

L   F   D   I   H   M   I   G   R   M   G   Y   R   L   N
  ACTATTCGATATTCATATGATTGGTCGAATGGGATATCGACTAAA
           170       180       190       200
```

FIG. 12

```
MDV   AATGTCTTTGAAGTCGAGCCCAATCGAGAACCATATTTTGTCTGTTATCAGAACTAGCAAGTCTCGTTGACAGATGCTCCAAATAAGTG
       T  K  Q  L  R  A  W  D  F  G  Y  K  Q  R  S  D  S  S  A  L  R  T  S  L  H  E  L  Y  T

MDV   GGAACCGACTCAATCGCACTCATAAAGTTAGTGGGATGAGAAATATTAGTCCCAGTTTTTGCATAGAATGCATATAAACAAGAATCGCA
       P  V  S  E  I  A  S  M  F  N  T  P  H  S  I  N  T  G  T  K  A  Y  F  A  Y  L  C  I  I  A

MDV   CATTCTAGAGAGGAATAATAAACGGGTGCCTACATAATAACGTTCCGTGATTGTAAAGATGTGATTGCCGTCACAATAACGTTCGGAC
       C  E  L  S  S  Y  Y  R  T  G  V  Y  L  R  G  C  S  Q  L  S  T  I  A  T  V  I  F  T  R  S

MDV   ATTCTTCCACCATGATAGTCTATTTTCTGGCAACGAGAGCATTTGTAAAGTACGATACCACGTGCCGAAA
       M  R  G  G  H  Y  D  I  K  R  A  V  S  P  K  D  V  A  L  A  N  Q  L  T  R  Y  W  T  G  F

MDV   ACGACACCGGAGTTCACTACACTTCCTATTTGCATAGACTAAGTTCAAGAGACAAATTAGAGTCGTATCTGAGCAAAGGATCA
       V  V  G  S  N  V  V  N  R  N  A  Y  V  L  N  L  L  D  V  S  L  N  S  D  Y  R  L  L  P  D

MDV   TTTTTCACGATTTGAATCTCACGGGCGAAGTGATATATTAACGCTCTTCCTTGTGCTGTCCAGATTTTCAACAGCACTAACGGCAATATCC
       N  K  V  I  Q  I  E  R  A  S  T  I  N  V  D  E  K  H  Q  G  S  K  E  V  A  S  V  A  I  D

MDV   ATTGCAGCGGTCGGCCAAGTTCTGCTGCAGCCGCTAACGTTCCAGTTGCCGATATATTCAATTTTTCTTCTTATTGGT
       M  A  A  D  A  L  E  A  A  A  A  H  E  L  D  A  L  A  T  A  I  Y  E  I  K  E  E  I  P
```

FIG. 14A

```
                   640       650       660       670       680       690       700       710       720
MDV   CGAAGTCTGCGGTCAATTCTATTGCAATAGAGTCGGTATGACCATCCAAATTATTAATGCTGCAGTGGCGCATTGTTCGTGCAGTA
       R  L  R  R  D  I  E  I  A  I  S  D  T  H  G  D  L  N  N  L  A  A  T  A  A  N  N  R  A  T 730       740       750       760       770       780       790       800       810
MDV   ATGATCGCAAGTTGTCGTTCCATATTGGCGCGGTTAGATGTAAATACCGGTTCCTTCCAGAACTCGATGGGCCATGGGGAGCTATAAAG
       I  I  A  L  Q  R  E  M  N  A  R  N  S  T  F  V  P  E  K  W  F  E  I  P  W  P  P  A  I  F 820       830       840       850       860       870       880       890       900
MDV   TTCTTCACATCGGCAGGGAACATTTCCATTCCATCGCCTGTCAATATTCTCGCGTCCCAAATAAAGTTGCCATGATGGTGCTACTCGAT
       N  K  V  D  A  P  F  M  E  M  G  D  G  T  L  I  R  A  D  W  I  F  N  A  M 910       920       930       940       950       960       970       980       990
MDV   ATAATCAGAGACAAGTTACAGGGAAACGCCACACATGAGAAATAATACTAAACATTTAAACTTAAAAGTGTTACGGTCTCTG
                                                                                       .  P  R  Q 1000      1010      1020      1030      1040      1050      1060      1070      1080
MDV   AACAAGACGGGCGATAATAGCCATGTTTGCATAGCCGTACCTCCCGTTCTCCTGATTATTGAAAATGATAAAGTAGCCGTTTT
       V  L  R  A  I  I  N  A  M  N  R  M  A  T  G  G  T  R  E  Q  N  N  F  S  L  T  A  T  K 1090      1100      1110      1120      1130      1140      1150      1160      1170
MDV   ATTACAAGCTATATGATTCCTCAAATCCGTTACGTTAGCAGAGACGCCTTCCACTGGCGTCGTTGTATATGTCGTGTTTCTATTATGACG
       N  C  A  I  H  N  R  L  D  T  V  N  A  S  A  K  G  S  R  R  Q  I  H  I  T  N  T  N  H  R 1180      1190      1200      1210      1220      1230      1240      1250      1260
MDV   TTTTAAAATTTATGAGTGTCAGTTATCCGTGCTTATAGTCAGACGCGGTTCGCCAATAGAGAGCATAGCTATGAAAATCAGTCACTAT
       K  L  I  K  H  T  D  T  I  R  A  K  Y  D  S  A  T  A  L  I  S  C  L  R  H  F  D  T  V  I 1270      1280      1290      1300      1310      1320      1330      1340      1350
```

```
MDV  ATTCCCTCGGACCGATCTGGTCTTAAATTAGATGACAAAGAGGATCCTCTAGAT
          3520      3530      3540      3550      3560      3570      3580      3590      3600      3610
              L   N   P   G   Y   K   F   V   L   T   S   E   L   V   G   A   Y   T   K   R   S   C   F   V   D   P   M   D   S   L
HVT  CTCAACCCCGGATACAAGTTCGTTCTCACAAGCGAGTTGGTAGGAGCCTACACAAAACGATCTTGTTTTGTCGATCCGATGGATTCTC
          3620      3630      3640      3650      3660      3670      3680      3690      3700
              V   P   I   D   Y   D   H   V   R   T   I   I   F   G   S   A   G   M   E   I   L   M   K   M   G   I   T   L   A   S
HVT  GTCCCGATAGATTATGATCATGTACGAACCATTATATTCGGATCTGCTGGGATGGAGATTTTAATGAAGATGGGAATTACTTTGGCATCT
          3710      3720      3730      3740      3750      3760      3770      3780      3790
              M   T   I   S   T   K   Y   N   P   P   I   E   L   I   I   S   A   K   Y   R   N   L   S   L   L   W   P   P   R   Q
HVT  ATGACCATTTCGACGAAATATAATCCTCCTATTGAACTGATAATATCTGCAAAGTACCGAAATTTATCACTGTTGTGGCCACCCCGACAA
          3800      3810      3820      3830      3840      3850      3860      3870      3880
              Q   Y   E   P   V   N   K   G   T   G   R   P   H   W   I   Y   L   L   G   V   Y   R   N   V   S   D   S   E   R   D
HVT  CAATATGAACCTGTAAATAAAGGGACTGGACGCCCCCATTGGATCTATCTATTAGGAGTGTATAGAAACGTTTCGGACTCCGAGCGTGAC
          3890      3900      3910      3920      3930      3940      3950      3960      3970
              S   Y   M   N   M   I   K   S   L   G   D   S   M   D   Y   H   F   L   I   S   R   A   H   A   Q   M   L   I   L   A
HVT  TCATACATGAATATGATTAAGAGTCTCGGGGCGATTCTATGGATTATCACTTCCTAATTAGCAGAGGCCATGCCCAGATGCTGATACTGGCA
          3980      3990      4000      4010      4020      4030      4040      4050      4060
              A   E   D   R   L   V   D   E   M   H   S   F   R   N   V   I   A   R   L   F   V   S   L   F   A   F   I   R   N   A
HVT  GCAGAGGACCGGCTCGTTGATGAAATGCATAGTTTCAGGAACGTTATTGCCGCGTTTATTTGTTGTATCGTTCATTCATACGCTAACGCA
          4070      4080      4090      4100      4110      4120      4130      4140      4150
              F   Q   S   G   Y   T   S   L   N   D   I   I   E   I   E   A   D   L   R   L   I   V   E   G   I   S   S   A   A   F
HVT  TTTCAGTCTGGCTACACCTCTCTTAATGACATAATTGAAATCGAAGCCGATTTGAGGTTAATTGTAGAAGGCATTTCTTCTGCTGCATTT
          4160      4170      4180      4190      4200      4210      4220      4230      4240
```

*FIG. 14E*

```
        R   K   D   A   S   T   H   F   L   I   K   S   G   T   P   I   K   D   S   K   A   D   L   I   K   S   L   L   S   K   V
HVT    CGTAAAGACGCTAGTACACACTTTCTTATATCGGGAACGCCCATAAAAGATAGCAAAGCGGATTTAATTAAATCGTTGTTGTCTAAAGTC
            4250            4260            4270            4280            4290            4300            4310            4320        4330

I   R   P   I   S   G   H   T   R   P   L   S   A   I   Q   H   L   F   L   L   R   S   A   Y   A   L   D   I   P   R
HVT    ATTCGACCAATTTCCGGACATACACGTCCCTTATCTGCGATACAACACATCTATTCCTTTGAGATCCGCTTATGCATTGGATATACCCCGT
            4340            4350            4360            4370            4380            4390            4400            4410        4420

Q   N   G   S   L   S   E   Q   V   S   T   V   A   L   S   F   I   E   N   I   H   S   E   A   M   R   D   I   L   S
HVT    CAAAACGGATCTTTGAGCGAACAAGTATCTACAGTGGCACTGTCGTTCATTGAAAATATTCACAGCGAGGCCATGAGGGACATTCTGTCA
            4430            4440            4450            4460            4470            4480            4490            4500        4510

W   N   T   T   K   H   A   L   Y   Y   A   F   A   S   I   L   Q   R   P   L   T   E   W   G   A   S   R   N   A
HVT    TGGAACACTACAACAAAGCATGCGTTGTATTATGCATTTGCAAGCATTTTGCAACGGCCACTGACCGAATGGGGCGCCTCAAGAAATGCA
            4520            4530            4540            4550            4560            4570            4580            4590        4600

R   R   A   I   L   L   A   S   S   M   C   T   E   E   H   V   I   A   T   E   L   A   I   Q   E   L   Y   V   K   I
HVT    CGGAGGGCAATACTACTAGCATCATCGATGTGTACAGAGAGCATGTGGCTATTCAAGAACTGGCTATTCAAGAACTGTATGTCAAAATC
            4610            4620            4630            4640            4650            4660            4670            4680        4690

R   S   N   A   D   P   I   H   L   L   D   V   Y   T   P   C   L   S   S   L   R   L   D   L   S   E   H   H   R   I
HVT    AGAAGTAATGCCGACCCAATACACCTTCTAGACGTATATACACCATGTCTTCTTCACTAGATTGGACCTTTCGAACACCATCGGATA
            4700            4710            4720            4730            4740            4750            4760            4770        4780

Y   A   M   A   D   V   F   Y   P   D   I   Q   Q   Y   L   K   K   K   S   H   E   G   N   M   K   E   D   D   L
HVT    TACGCAATGGCAGATGTAGTTTTCTATCCAGACATTCAGCAGTATTTGAAAAAAAAATCCCATGAGGTAATATGAAGGAAGATGATCTC
            4790            4800            4810            4820            4830            4840            4850            4860        4870
```

*FIG. 14E-1*

```
         E  T  K  A  E  Y  I  L  T  K  L  R  S  P  L  I  R  T  L  S  A  Y  A  S  E  V  L  S  C  S
HVT   GAAACAAAGGCGGAATACATCCTCACCAAGCTTAGGTCGCCGTTGATCAGAAGCTGCTATGCATCAGAAGAAGTATTGTCCTGCTCC
                 4880         4890         4900         4910         4920         4930         4940         4950         4960

D  Q  D  L  E  I  N  A  I  L  L  P  V  S  G  I  G  S  Y  V  V  S  R  R  A  G  M  Q
HVT   GACCAGGATCTAGAAATAAATGCTATTTTAATTCTGCCCGTTTCCGGTATTGGGAGCTATGTAGTCTCGAAGGCAGGAATGCAA
                 4970         4980         4990         5000         5010         5020         5030         5040         5050

G  I  V  Y  T  V  D  G  V  D  V  N  N  Q  L  F  I  T  Y  T  R  M  P  C  T  T  T  I  G  N
HVT   GGCATTGTTTATACCGTAGACGGTGTTGATGTTAACAATCAGTTTTTTATAACATATACCAGGATGCCGTGCACTACAACGATAGGTAAC
                 5060         5070         5080         5090         5100         5110         5120         5130         5140

I  V  P  T  V  L  S  R  P  S  G  K  T  C  P  Y  C  G  C  V  L  R  Y  S  A  D  G  N  I
HVT   ATTGTTCCAACAGTATTGTCAAGACCCTCGGGAAAAACGTGTCCGTATTGCGGGCTGTGTTTTGCTGCGATATTCCGCCGATGGAAATATC
                 5150         5160         5170         5180         5190         5200         5210         5220         5230

R  Y  S  I  Y  I  S  S
HVT   CGCTATTCTATTTACATTTCGTCCC
                 5240         5250
```

*FIG. 14F*

```
G  R  R  K  Y  D  A  L  V  A  -  F  V  L  G  R  A  C  G  R  P  I  Y  L  R  E
GGGACGACGCAAATATGATGCTCTAGTAGCATCTTGTCTTGGGCAGAGACCATGTGGGAGACCAATTATTTACGTGAA

Y  A  N  C  S  T  N  E  P  F  G  T  C  K  L  K  S  L  G  W  D  R  R  Y  A
TATGCCAACTGCTCTACTAATGAACCATTTGGAACTTGTAAATTAAAGTCCCTAGGATGGTGGGATAGAAGATATGCAA

M  T  S  Y  I  D  R  D  E  L  K  L  I  A  A  P  S  R  E  L  S  G  L  Y  T  R
TGACGAGTTATATCGAGATGAATTGAAATTGATTATTGCAGCACCCAGTCGTGAGCTAAGTGGATTATATACGCG

L  I  I  N  G  E  P  I  S  S  D  I  L  L  T  V  K
TTTAATAATTATTAATGGAGAACCCATTTCGAGTGACATATTACTGACTGTTAAA
```

*FIG. 15*

VIRAL NUCLEOTIDE SEQUENCES

This is a division of application Ser. No. 08/460,257 filed Jun. 2, 1995, U.S. Pat. No. 5,965,435 which is division of Ser. No. 08/125,039 filed Sep. 22, 1993, U.S. Pat. No. 5,906,821 which is a continuation of Ser. No. 07/669,391 filed Apr. 29, 1991, abandoned; which is a 371 of PCT/GB89/01075 filed Sep. 13, 1989.

The present invention relates to viral nucleotide sequences which may be manipulated to provide vaccines against disease.

BACKGROUND AND DESCRIPTION OF PRIOR ART

Herpesviruses are large double stranded DNA viruses consisting of an icosahedral capsid surrounded by an envelope. The group has been classified as alpha, beta and gammaherpesviruses on the basis of genome structure and biological properties [Roizman, B. et al (1981) Intervirology 16, 201–217]. Avian herpes viruses include Marek's Disease Virus (MDV) (a gammaherpesvirus) which causes a lymphomatous disease of considerable economic importance in chickens [reviewed in Payne, L. N. (ed) Marek's Disease (1985), Martinus Nijhoff Publishing, Boston] and Infectious Laryngotracheitis Virus (ILTV) (an alphaherpesvirus) which causes an acute upper respiratory tract infection in chickens resulting in mortality and loss of egg production.

A recent unexpected finding in out laboratory is that there is sufficient amino acid homology between MDV, ILTV and mammalian herpesviruses, particularly varicella zoster (VZV) and Herpes Simplex virus (HSV) to allow identification of numerous conserved genes. These include the MDV and Herpesvirus of Turkeys (HVT) homologues or glycoproteins gB, gC and gH of HSV; the ILTV, MDV and HVT homologues of TK and ribonucleotide reductase genes and the ILTV homologue of gB and genes 34 and 35 of VZV [Buckmaster, A et al, (1988) J. gen. Virol, 69, 2033–2042.

Strains of MDV have been classified into three serotypes. Type 1 comprises pathogenic strains and their attenuated derivatives. Type 2 are a group of naturally-occurring non-pathogenic strains and type 3 is HVT. For more than a decade, vaccination with HVT has been remarkably effective in controlling Marek's disease. However, in recent years, new strains of MDV have been isolated which cause disease despite vaccination with HVT. Losses due to these 'very virulent' strains have occurred in parts of the U.S.A., Europe and the Middle East. Although the degree of protection can be improved by using a mixture of HVT, type 2 MDV and attenuated derivatives of very virulent strains for vaccination, the results have been erratic. These observations and the fact that there are MDV type-specific epitopes that are not shared by HVT or type 2 MDV have led us to the conclusion that improved vaccines might be constructed which are antigenically more related to MDV than existing vaccines. [Reviewed by Ross and Biggs in Goldman J. M. and Epstein M. A. (eds) Leukaemia and Lymphoma Research, Vaccine Intervention against Virus-Induced Tumour, p 13–31, Macmillan, 1986.]

Infectious laryngotracheitis is also a worldwide problem. Sporadic outbreaks occur in which the severity of clinical symptoms varies considerably. Virus can persist in birds that have recovered and may be shed at intermittent intervals after recovery. An attenuated field strain is currently used as a vaccine. However, it has retained some degree of pathogenicity. Mortality due to the vaccine may reach 10% in young chicks.

A number of herpesvirus antigens have been shown to confer protective immunity when expressed in a recombinant vaccinia virus. These include the gB gene of HSV (Cantin E. M. et al (1987) Proc. Natl. Acad. Sci. U.S.A. 84, 5908–5912], gD of HSV [Paoletti, E. et al (1984) Proc. Natl. Acad. Sci. U.S.A. 81, 193–197] and gp50 of pseudorabies virus (PRV), a homologue of HSV gD [Marchioli, C. C. et al (1987) J. Virol. 61, 3977–3981]. Because of the absolute requirement of gB for virus penetration and infectivity and because it is conserved among herpes-viruses, gB and its homologues are important immunogens. Moreover, the presence of gB at the surface of infected cells has been shown to be an important target for humoral and cell-mediated immune responses [Blacklaws, B. A. et al J.gen. Virol. 68, 1103–1114 (1987); McLaughlin-Taylor, E. et al (1988) J. gen. Virol. 69, 1731–1734]. The recently described glycoprotein gH of HSV is also essential for infectivity and may also be an important immunogen [Desai, P. J. et al (1988) J. gen. Virol. 69, 1147–1156]. It has also been shown that gIII of pseudorabies virus (PRV), a homologue of gC, is a major target for neutralizing antibody and for cytotoxic T cells although it is a non-essential protein. Also of interest is the unexpected participation of immediate early proteins in T cell mediated cytotoxic reactions in cells infected with cytomegalovirus (CMV) [Kozinowski U. H. et al (1987) J. Virol. 61, 2054–2058]. Similar antigens could play an important role in the rejection of latently infected and transformed lymphocytes in Marek's disease since immediate early RNA transcripts have been detected in lymphoblastoid cell lines established from Marek's disease tumours.

Although many recombinant vaccines have been constructed using the poxvirus vaccinia as a vector, there are also reports of the use of herpesviruses as vectors for the expression of foreign genes. Thus hepatitis antigen has been expressed in HSV [Shih, M. F. et al (1984) Proc. Natl. Acad. Sci. U.S.A. 81, 5867–5870] and human tissue plasminogen activator has been expressed in PRV [Thomsen, D. R. et al (1987) Gene 57, 261–265. In both cases, foreign genes were inserted in cloned fragments of non-essential herpes genes which were then introduced into the virus vector by homologous recombination. The hepatitis virus gene was fused to a herpesvirus promoter and the recombinant DNA was inserted within the TK gene of HSV. Homologous recombination following co-transfection of the recombinant DNA and wild-type HSV DNA resulted in TK⁻ virus clones that expressed the hepatitis antigen.

In the case of PRV, the gX gene mapping in $U_s$ was used as the site for insertion of the foreign gene. The strategy used involved insertion of the TK gene of HSV in the gX gene of a PRV mutant that had a defect in its TK gene resulting in a TK positive virus. The human tissue plasminogen activator gene was then inserted within a cloned fragment of HSV TK and the recombinant was introduced into the PRV mutant by homologous recombination. TK⁻ virus was selected which expressed the human gene (Thomsen et al as above). Similarly, VZV has been used as a vector [Lowe et al (1987) Proc. Natl. Acad. Sci. U.S.A. 84, 3896–3900].

Several herpesvirus genes have also been shown to be associated with virulence and to be non-essential for growth in vitro. These include the TK genes or HSV [Jamieson, A. T. et al (1974) J. gen. Virol. 24, 465–480; Field, H. and Wildy, P., (1987) J. Hygiene (Cambridge) 81, 267–277] and of PRV. Indeed it has long been known that PRV is readily attenuated by deletion of TK activity [Tatarov, G. (1968) Zentralbl. Vet. Med 15B, 848–853]. Furthermore, attenuation of the Bartha strain of PRV has been attributed to a defect in gI, a non-essential structural glycoprotein mapping in $U_s$ [Mettenleiter, T. et al (1987) J. Virol. 61, 4030–4032].

Genes of HSV mapping in the internal repeat region (TRS) flanking the long unique sequence have also been associated with pathogenicity [Rosen, A. et al (1986) Virus Research 5, 157–175; Thompson, R. L. et al (1983) Virology 131, 180–192]. Several additional genes of HSV have been shown to be non-essential for growth in vitro although it is not known whether they are associated with virulence. These include UL24 (Sanders, P. G., (1982), J. gen. Virol. 63, 277–295, large subunit of ribonucleotide reductase (Goldstein D. J. and Weller, S. K. (1988) J. Virol. 62, 196–205), gC (Draper K. G. et al (1984) J. Virol. 51, 578–585), dUTPase (Fisher, F. B. & Preston, V. G. (1986) Virology 148, 190–197), and $U_L55$ and $U_L$ 56 (MacLean, A. R. & Brown, S. M. (1987) J. gen. Virol. 68, 1339–1350).

Moreover there is evidence that several genes of (HSV mapping in $U_s$ are also non-essential for growth in vitro [Weber, P. C. et al (1987) Science 236, 576–579].

SUMMARY OF THE INVENTION

One aspect of the present invention provides a nucleotide sequence substantially free of the sequences which would adjoin it in the wild-type virus associated with the sequence, the sequence being selected from the group consisting of:
(a) the HVT homologue of the HSV gB gene,
(b) the HVT homologue of the HSV gC gene,
(c) the HVT homologue of the HSV gH gene,
(d) the TK gene of ILTV,
(e) the ILTV homologue of the HSV gB gene,
(f) ORF2 of ILTV,
(g) ORF3 of ILTV,
(h) the ribonucleotide reductase (large subunit) gene of ILTV,
(i) the ribonucleotide reductase (large subunit) gene of HVT,
(j) the ribonucleotide reductase (large subunit) gene of MDV,
(k) the ribonucleotide reductase (large subunit) gene of MDV,
(l) the HVT homologue of the immediate early gene IE-175 of HSV-I, and
(m) the RVT homologue of the immediate early gene IE-68 of HSV-I,
and minor variations thereof.

Each of sequences (a) to (m) may be associated with further elements such as suitable stop and start signals and other 5' and 3' non-coding sequences, including promoters, enabling expression of the sequence. Such further elements may be those associated with the sequence in its naturally-occurring state or may be heterologous to that sequence.

In particular the promoter may be one associated with one of the sequences (l) and (m) above.

The term "minor variations thereof" is intended to include changes in the nucleotide sequence which do not affect its essential nature, for example minor substitutions of nucleotides for one another. In the case of sequences which are intended for insertion into a vector to encode an antigen, the "essential nature" of the sequence refers to the (glyco) protein encoded. Conservative changes in the nucleotide sequence which give rise to the same antigen will clearly be included, as will changes which cause conservative alterations in the amino acid sequence which do not affect adversely the antigenic nature of the antigen, in particular, antigenic portions of the antigen sequences may be used alone, for example the regions corresponding to nucleotides 273–320 or 867–926 of HVT gH and minor variations thereof. These sequences and the peptides encoded thereby form a further aspect of the invention. In the case of a sequence which is an insertion site, it is necessary only that the sequence should be non-essential for the infectivity and replication of the virus and have sufficient homology with the defined sequence to enable recombination to occur. Thus an insertion of one nucleotide into the sequence could completely change the reading frame from then on in a downstream direction. In the case of an antigen-encoding sequence this would usually alter the amino acid sequence undesirably (depending on where the frameshift occurred), but in the case of an insertion site, the degree of homology would be almost the same, thereby allowing recombination to take place with almost the same ease.

Generally speaking, in an insertion site, if a nucleotide homology of at least 75% is present, the sequence is regarded as a "minor variation". Preferably, the sequence is at least 80, 85, 90, 95 or 99% homologous.

It will be appreciated that such degrees of homology relate to substantially the entire portion of each sequence (a) to (m) defined above. Shorter sequences may be used as probes in the identification or isolation of such longer sequences, but in this case the degree of homology will in general need to be greater in order to ensure accurate hybridisation.

Thus, a further aspect of the invention provides sub-sequences of at least 13 nucleotides having at least 90% (preferably 95%, 99% or 100%) homology with at least one portion of any of the said sequences (a) to (m) above.

In the above list, sequences (a) to (c), (e), (f), (l) and (m) are useful for expressing viral antigens. Sequences (b), (d) and (g) to (k) and, in addition, the TK region of MDV are useful as non-essential sites suitable for insertion of antiaen-expressing genes. Thus, sequence (b) is useful for both functions.

The sequences may readily be isolated from naturally-occurring ILTV, HVT and MDV viruses, using the sequence information given herein and standard techniques, for example involving the preparation of oligonucleotide probes and use thereof to hybridise to the naturally-occurring DNA.

Antigenic ILTV and HVT sequences, i.e. sequences (a) to (c), (e), (f), (l) and (m) above, may be expressed in any suitable host and, in particular, in HVT or MDV. Suitable non-essential sites for insertion of one ILTV sequence include the MDV homologue of the HSV gC gene, the HVT homologue of the HSV gC gene, the TK gene of HVT or MDV, the ribonucleotide reductase (large subunit) gene of HVT or MDV and the ribonucleotide reductase (small subunit) gene of MDV.

A second aspect of the invention provides insertional or deletional mutants of MDV, HVT and ILTV as follows:
(i) for HVT, a mutation in the region homologous to the HSV gC gene or in the ribonucleotide reductase gene or the TK gene,
(ii) for MDV, a mutation in the region homologous to the HSV gC gene or in the ribonucleotide reductase (small subunit) gene or in the ribonucleotide reductase (large subunit) gene,
(iii) for ILTV, a mutation in the TK gene, ORF3 or the ribonucleotide reductase (large subunit) gene.

Each mutation may be in the coding or non-coding sequences of the regions identified.

Such mutant forms of HVT, MDV and ILTV may be used as, or created in the course of preparing, viral vectors for heterologous antigen-encoding sequences, or indeed as vectors for any other sequence which one wishes to express in a fowl in which the vector will replicate. Such sequences include, but are not limited to, (a) to (c), (e), (f), (l) and (m).

By "heterologous", we mean that the antigen-expressing sequence has not previously been found in the same place in relation to the remainder of the viral genome. For example, an antigen-expressing gene might be isolated from a virulent strain of ILTV and inserted into the TK region of a less virulent strain of ILTV; this insertion would be regarded as "heterologous" if it did not result in a naturally-occurring virus.

The heterologous sequence may alternatively be one coding for an antigen associated with any one of the following diseases: avian encephalomyelitis (epidemic tremor), avian influenza (fowl plague), avian leukosis, avian paramyxoviruses other than Newcastle disease (PMV2 to PMV7), avian reovirus diseases (enteric disease, tenosynovitis), chicken anaemia (caused by chicken anaemia agent), coccidiosis, egg drop syndrome (EDS76), fowl pox, infectious bronchitis, infectious bursal disease (Gumboro), inclusion body hepatitis (adenovirus), lymphoproliferative disease of turkeys, Newcastle disease, reticuloendotheliosis in chickens, reticulo-endotheliosis in turkeys, rotavirus enteritis, turkey haemorrhagic enteritis and turkey rhinotracheitis. The sequence may alternatively encode paramyosin (a muscle protein common to all invertebrate parasites) or an antigenic part thereof, somatostatin or a growth-promoting part thereof or an immune regulator.

The vectors in accordance with the invention may provide multivalent vaccine protection. For example, a vaccine comprising ILTV carrying an MDV antigen coding sequence would be expected to protect against ILT and Marek's Disease.

Furthermore, the mutant ILTV viruses themselves are potentially useful in vaccines as attenuated viruses, without necessarily having a heterologous sequence inserted.

A convenient process for preparing the deletional or insertional mutants of the second aspect of the invention comprises simply introducing into a suitable cell, for example by co-transfection, a deletional or insertional mutant version of the appropriate region (for example, the TK region) and either whole viral DNA or a whole virus (for example the wild-type virus). The naked DNA of such viruses has been found to be infectious, provided that it has not been sheared. A calcium phosphate precipitate of the DNA is generally advantageous. Suitable cells include chicken embryo fibroblasts, chicken kidney cells and duck embryo fibroblasts, all preferably grown in sub-confluent monolayers in Petri dishes.

The transfected DNA and the whole viral DNA will then recombine with one another in the infected cells by homologous recombination and the desired recombinants can be screened for, for example by the detection or hybridisation to suitable probes or by an immunoassay using suitable antibodies to the gene product of the region in question.

For homologous recombination to take place, the viral DNA must replicate. At present, no cell-free replication system for MDV, HVT or ILTV is known. However, if such a system becomes available, then the process of the invention could be operated therein. The environment in which the replication and recombination occur is not critical.

The ILTV and HVT regions which were identified above as being responsible for encoding immunologically useful viral antigens can be inserted into suitable vectors, for example into HVT or into other vectors such as fowlpoxvirus, bacteria or fungi. In the case of viral vectors, especially herpesvirus vectors and poxvirus vectors, such insertion can be achieved by recombination between the antigen-encoding sequence, flanked by suitable non-essential sequences, and the vector's genome in a suitable host cell as described above. A promoter which is endogenous to the host will usually be used to control expression of the heterologous (viral antigen-encoding) sequence. In the case of bacteria and fungi, the antigen-encoding sequence may be inserted using known or yet-to-be-discovered techniques of DNA manipulation. A non-pathogenic strain of Salmonella may be used as such a host. The heterologous sequence may be inserted into the host's genome or be carried on an independently-replicating plasmid.

The flanking sequences which are used may comprise all, virtually all or less of the region into which the heterologous sequence is to be inserted. If all the region is employed, then the sequence of that region will clearly still be present in the resulting virus, but the function of that region will have been deleted. If less than the whole region is used as flanking sequences, then the result will be a structural as well as functional deletion. Either approach may be used.

Thus, the construction of deletional or insertional mutants of ILTV can yield improved vaccines. Alternatively, the expression of ILTV glycoproteins or other ILTV proteins engineered into HVT, fowl pox or other vectors can constitute effective vaccines.

To prepare a vaccine in which HVT, MDV or ILTV is the virus or vector, the virus is grown in suitable cells such as chick embryo fibroblasts in a standard culture medium which as 199 medium (Wellcome or Flow Laboratories) for 3 to 4 days at about 37° C. The cells are harvested by scraping from the surface of the culture or by trypsinisation and suspended in medium containing 1 mM EDTA or 10% dimethyl sulphoxide and in either case 4% calf serum before storage in liquid nitrogen in sealed ampoules.

For vaccination, typically, day-old chicks are injected intramuscularly with about 1,000 plaque-forming units. Immunity follows within a few days.

It should be noted that MDV and HVT are cell-associated viruses and are infectious only when present in cells. Thus, a vaccine based on such viruses will always include suitable infected cells.

The vaccines of the invention may be used to protect any fowl susceptible to ILTV or HTV, including commercially-reared poultry such as chickens, turkeys, ducks and quail.

BRIEF DESCRIPTION OF THE DRAWINGS

Preferred aspects of the invention will now be described by way of example and with reference to the accompanying drawings, in which:

FIGS. 2A–2R (on 18 sheets) shows the nucleotide sequence of the gB gene of the RBIB strain of MDV, with the numbering referring to the MDV nucleotides, the sequence of part of the HVT gB gene shown under the line, homologies indicated by vertical bars, and amino acid differences between MDV gB and HVT gB shown above the line;

FIGS. 4A–4H (on 8 sheets) shows the nucleotide sequence of most of the HVT gH gene, with the corresponding amino acid sequence shown above the line;

FIGS. 5A–5J (on 10 sheets) shows the nucleotide sequence of the HVT TK gene, with the numbering referring to the HVT nucleotides, the sequence of part of the MDV TK gene shown under the line, homologies indicated by vertical bars and amino acid differences between MDV TK and HVT TK shown above the line;

FIGS. 6A–6F (on 6 sheets) shows the nucleotide sequence of the gC gene of the RBIB strain of MDV, with corresponding amino acids shown above the line;

FIGS. 7A–7K (on 11 sheets) shows the nucleotide and predicted amino acid sequence of a 5400 base pair region of the ILTV genome containing the TK gene cluster. Amino acid sequences predicted for the products of the major open reading frames (ORFs) are indicated in the single letter code below the sequence for the strand and above the sequence for the complementary strand. The locations of potential 'TATA' boxes are underlined. ORF 4 is the ILT TK gene sequence;

FIG. 8 is a representation of the gene organisation in the TK-containing part of the ILTV genome. Overlapping pUC 13 plasmid clones containing the EcoR1 (pILEc1) and BglII (pILBg2) generated fragments of ILTV DNA are indicated. Open reading frames (ORFs) are depicted as open boxes with the direction of transcription indicated by the arrow;

FIG. 9 shows part of the nucleotide sequence of the ILTV gB gene;

FIG. 10 shows part of the nucleotide sequence or the ILTV ribonucleotide reductase (large subunit), FIG. 11 shows part of the nucleotide sequence of the HVT homologue of the VZV62/HSV-1 IE 175 gene;

FIG. 12 shows part of the nucleotide sequence of the HVT riqonucleotide reductase (large subunit) gene;

FIGS. 14A–14F show part of the nucleotide sequence of the MDV ribonucleotide reductase (small subunit gene).

FIG. 15 shows part of the nucleotide sequence of the MDV homologue of the HSV-1 IE-175 gene;

EXAMPLES

General Approaches

Figure 1:
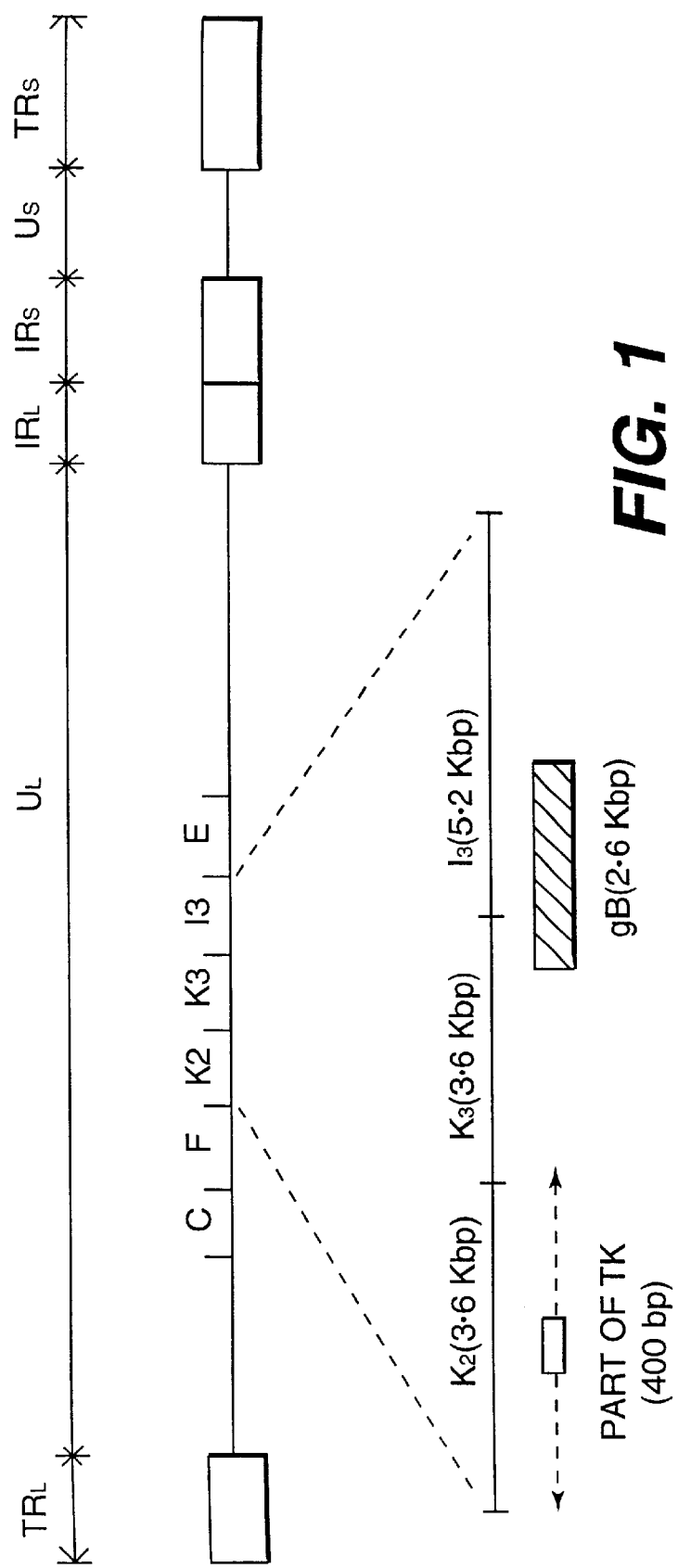
FIG. 1 is a map of the MDV genome showing in part the BamHl site distribution and the location of the gB and TK genes.
Figure 3:
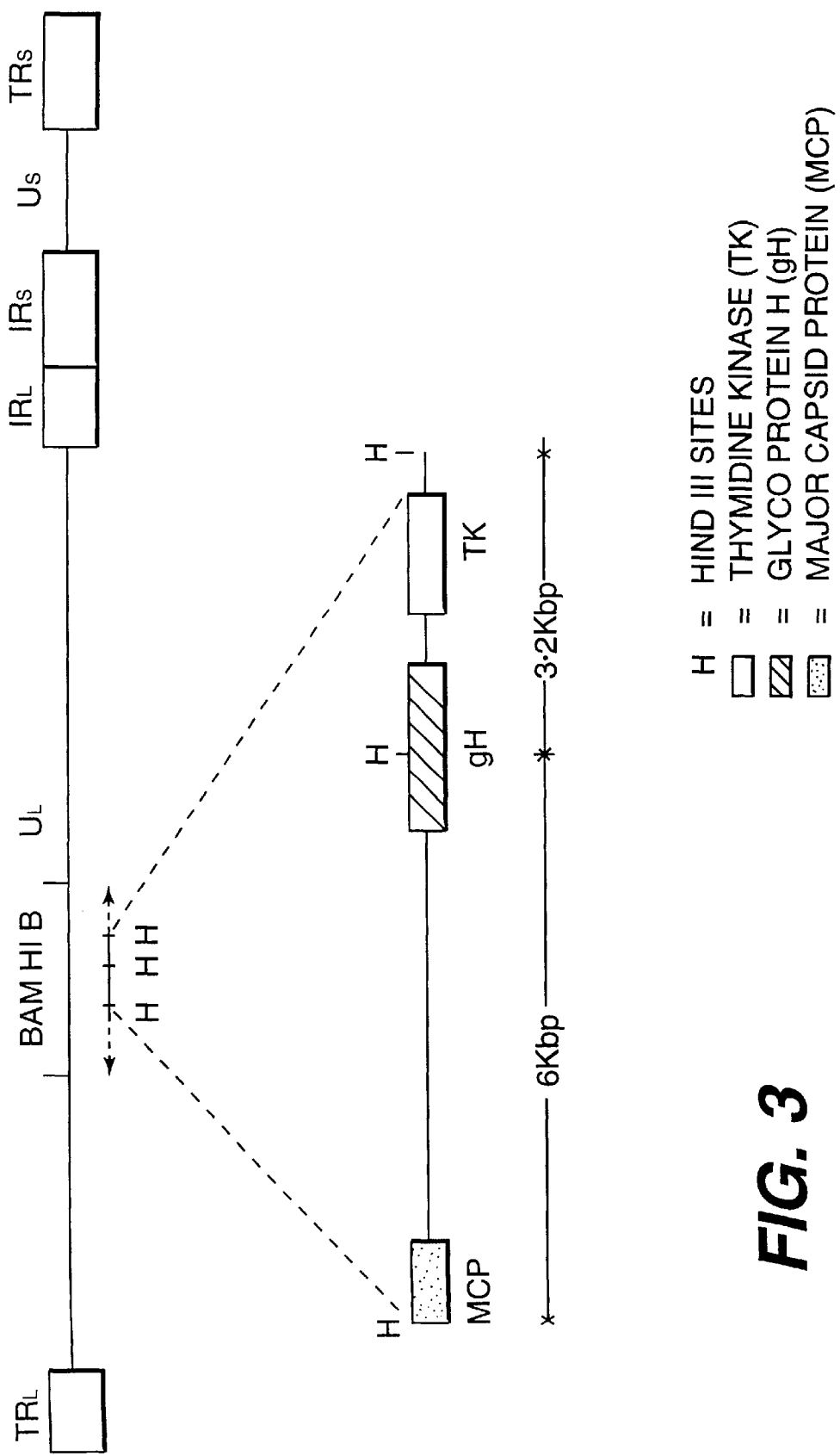
FIG. 3 is a map of the HVT genome showing the positions of the gH (hatched), TK (solid black) and major capsid protein (MCP, dotted) genes, with HindIII sites shown as "H"
Figure 13:
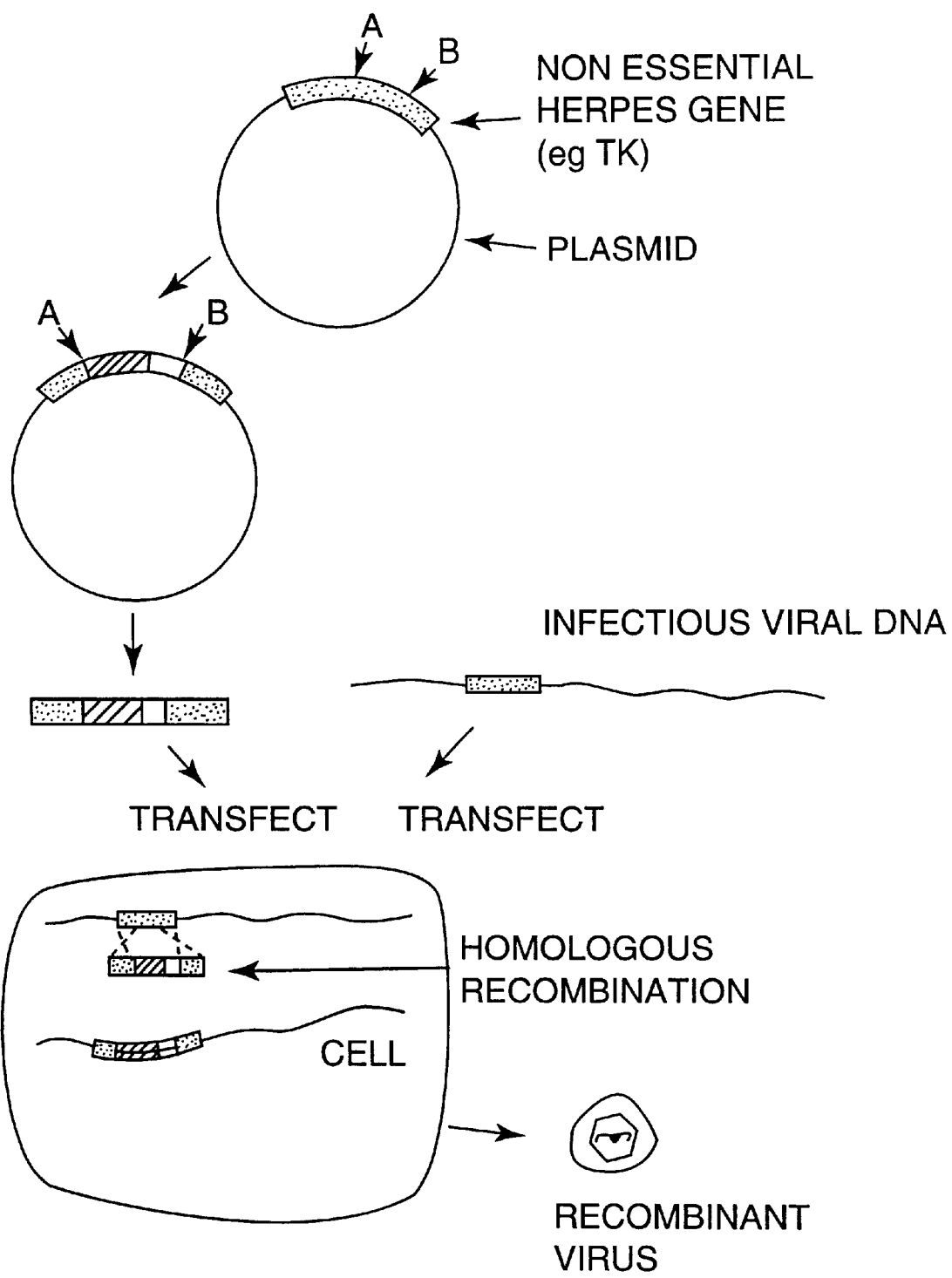
FIGS. 13A–13B shows part of the nucleotide sequence of the MDV ribonucleotide reductase (large subunit) gene.
Figure 16:
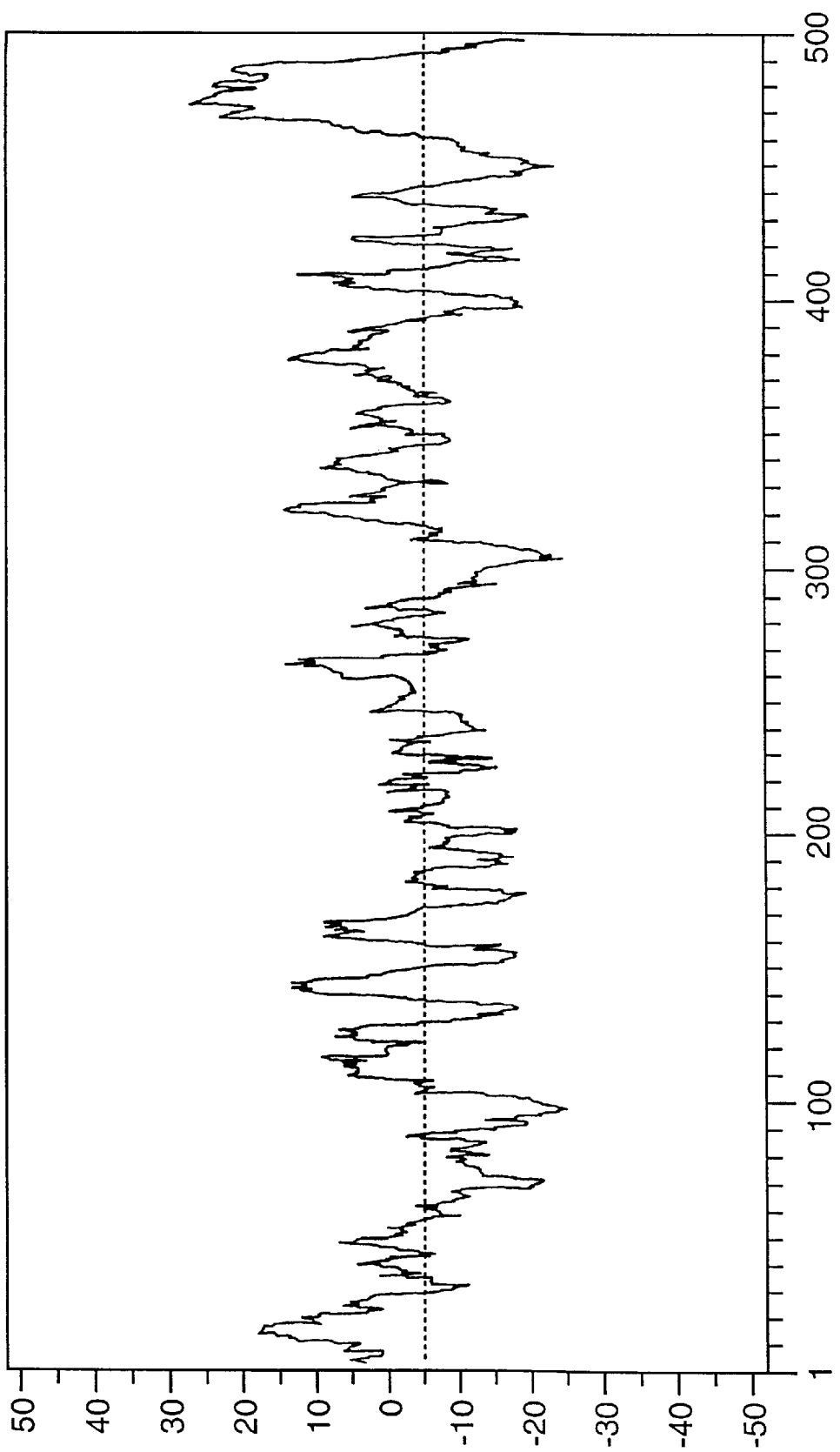
FIG. 16 shows part of the MDV homologue of the HSV-1 IE-68 gene.
Figure 17:
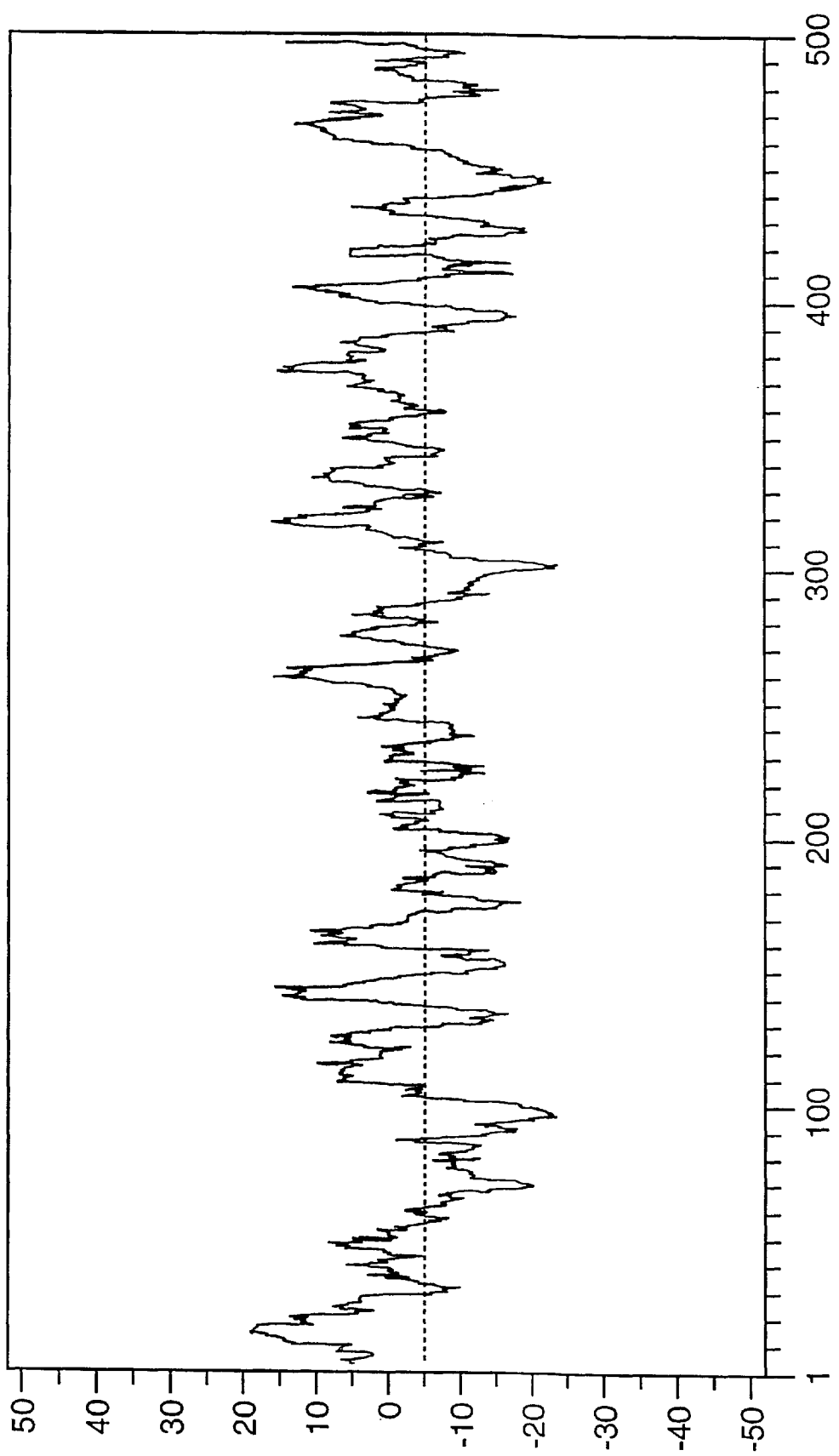
FIG. 17 is a schematic representation of homologous recombination at a non-essential region of a viral aenome and a homologous region of DNA cloned within a plasmid vector.

Selected short sequences of the avian herpesviruses cloned in the bacteriophage vector M13 were used as probes to identify longer fragments that might contain the entire genes of interest. This was achieved by Southern blot hybridization of restriction fragments. Full details are given below.

Virus Strains. The 'highly oncogenic' strain RB1B of MDV [Schat, K. A. et al (1982) Avian Pathol. 11, 593–6051] was obtained from Professor B. Calnek, Cornell University, Ithaca, U.S.A. The virus received has been plaque purified in chicken kidney vells in tissue culture. It was passaged twice in SPF RIR chickens and 4 times in chick embryo fibroblasts (CEF). Its 'highly oncogenic' nature was demonstrated by a high incidence of gross tumours when inoculated in genetically resistant N-line chickens.

The FC126 strain of HVT [Witter, R. L. et al (1970) Am. J. Vet. Res. 31, 525–538], obtained from the Wellcome Research Laboratories, Beckenham, Kent, had been passaged 14 times in CEF. It was subsequently grown in duck embryo fibroblasts (DEF) and CEF in our laboratory. It was then plaque-purified and grown further in CEF. Viral DNA used for cloning in the present work was extracted from virus that had been passed 29 times since the original isolation.

The Thorne strain of ILTV was passaged twice in eggs, once in chicken kidney cells (CKC) and plaque-purified three times in CKC.

Tissue culture. CEF were grown in roller bottles in 199 medium (Wellcome), supplemented with penicillin, streptomycin, Fungizone (Regd. T.M.) and calf serum as described previously [Ross, L. J. N. et al (1975) J. gen. Virol. 28, 37–47].

CKC were grown in 10 cm Petri dishes [Churchill, A. E. and Biggs P. M., (1967) Nature, 215, 528–530].

Isolation of MDV DNA. Cell associated RB1B was inoculated onto confluent monolayers of CEF in roller bottles at a multiplicity of infection of approximately 0.001 plaque-forming units (pfu) per cell, and the cultures were incubated at 37° C. After 3 days, the medium was discarded and replaced with fresh 199 medium containing 2% calf serum. Cells were harvested for virus purification after 2 to 3 days when cytopathic effect was extensive. Virus was obtained by rate zonal centrifugation of the cytoplasmic fraction of infected cells [Lee, Y. S. et al (1980) J. gen. Virol. 51, 245–253]. Viral DNA was extracted by treating purified virus with sarcosyl, proteinase K and Tris buffer pH 9 overnight at 37° C. and purified by rate zonal centrifugation in glycerol gradients as described previously (Lee et al, 1980). High molecular weight viral DNA was precipitated with ethanol and resuspended in 10 mM Tris pH 7.5 im 1 mM EDTA (TE).

Isolation of ILTV DNA. (a) Infected CKC were harvested 2–3 days after inoculation, washed in PBS, and resuspended in ice-cold TE by vortexing. Cells were lysed by addition of the non-ionic detergent NP40 (final 1%) vortexing and incubation on ice for 15 min. After treatment with RNAse, the preparation was centrifuged at 2000 rpm for 5 min in a bench top centrifuge (Centaur). The supernatant was collected and incubated at 37° C. for 30 min in the presence of SDS (final 1%) and proteinase K (final 0.5 mg/ml). The mixture was extracted twice with phenol-chloroform and once with chloroform and the DNA was then precipitated with ethanol and 1/10 vol of 3M sodium acetate.

(b) Viral DNA was also isolated from the media of virally infected cells in the following way. The media of infected cells were harvested at 2–3 days post infection and centrifuged at 3000 for 5 mins at 4° C. rpm in a bench centrifuge. The supernatant was collected and centrifuged at 19K rpm in an ultracentrifuge (Sorvall) for 1 hr at 4° C. The viral pellet was resuspended in TE, digested with RNAse A, then disrupted with SDS and proteinase K as described above. Finally, DNA was extracted from the disrupted. virus as described above.

Cloning of MDV DNA. One fg of MDV DNA was cut with the restriction enzyme BamH1 and ligated to BamH1-cut, dephosphorylated pUC13 DNA (Pharmacia). Competent E.coli strain TG1 cells were transformed according to standard procedures [Hanahan, D. (1983) J. Mol. Biol. 166, 557–580] and were grown in the presence of ampicillin and X-gal. White colonies were picked and tested for the presence or MDV inserts by hybridization to nick-translated MDV DNA [Grunstein M. and Hogness, D. S. (1975) Proc. Natl. Acad. Sci. U.S.A. 72, 3961]. Positive colonies were cultured in small volume and plasmid DNA isolated by the procedure of Holmes, D. S. and Quigley, M. [(1981) Anal.

Biochem. 114, 193–297]. The size of the inserts was determined by electrophoresis of BamH1 digests of the recombinant DNA in agarose gels. Plasmids containing MDV inserts ranging from less than 1 to 18 Kbp were obtained.

Cloning of ILTV DNA. EcoR1 and B1II libraries of ILTV DNA were obtained by cloning digests of viral DNA in pUC13 as described above.

Random sequencing of viral DNA. Sonicated fragments of viral DNA were cloned into SmaI-cut, dephosphorylated M13.mp10 (Amersham International PLC) and plaques containing MDV inserts were identified by hybridization to MDV DNA. The sequence was determined by the dideoxy method [Sanger, F. et al (1977) Proc. Natl. Acad. Sci. U.S.A. 74, 5463–5467] using $^{15}$S dATP).

The same procedure was used to sequence cloned fragments of MDV, HVT and ILTV DNA except that plaques were identified by hybridization to labelled insert so as to avoid colonies containing pUC13 fragments.

Example 1 gB Gene of MDV

An M13 clone of HVT homologous to the gB gene of VZV and HSV hybridized to BamH1 fragment I3 of MDV (see FIG. 1). Sequencing of this fragment obtained from a BamH1 library of the RB1B strain of MDV showed that two thirds of the gene, starting with the $NH_2$ terminus, was contained within I3. The remainder of the gene was identified in the adjacent restriction fragment K3. FIG. 1 shows the map position of the gene which is 2.6 Kbp long. Its mRNA has been estimated to be approximately 2.8 Kb. The translated protein is 865 amino acids long (FIG. 2). This includes approximately 20 amino acids which may be part of a signal sequence domain. The primary translated sequence of MDV gB has a few features in common with gB of other herpes viruses such as the alignment of cysteine residues and the presence of hydrophobic sequences which are presumably capable of spanning a lipid bilayer [Pellet, P. E. et al (1985) , J. Virol. 53, 243–253]. However, MDV gB has only 48% amino acid similarity with gB of HSV and has many unique features such as the insertion of 23 amino acids (residues 1851–1920, FIG. 2) and the presence of extra sites with glycosylation potential. Comparison of the sequence of MDV gB with limited sequence data (702 bases) available for HVT gB (FIG. 2) has shown 76.9% nucleic acid similarity and 87.1% amino acid similarity between these two glycoproteins. Amino acid substitutions in HVT gB compared to MDV gB were particularly marked in a region (residues 1323–1433) equivalent to a domain of HSV gB associated with virus neutralization [Pellet P. E. et al (1985) as above]. Amino acid substitutions between MDV and HVT gB were also noted in other regions of unknown function.

Example 2 gH Gene of HVT and gH Gene of MDV

An HM13 clone of HVT containing sequences homologous to HSV gH was isolated during our earlier work on gene identification and mapping (Buckmaster et al (1988) as above). This clone, when used as a probe, hybridized to a 6 Kbp HindIII fragment of HVT (FIG. 3). Sequencing revealed that this fragment contained approximately one quarter of the gH gene including the carboxy terminus. The adjacent HindIII fragment (3.2 Kbp) containing the remainder of the gH gene was identified by hybridization using a cloned HpaI fragment of HVT which overlapped the HindIII site. FIG. 4 shows the sequence of the coding region of the gH gene of HVT (2.3 Kbp) and flanking sequences. The % amino acid identity between the gH gene of HVT and its homologue in HSV1, VZV and EBV was only 20, 24 and 20 respectively (estimated from maximised amino acid overlaps of 630, 644 and 153 respectively).

Example 3

TK Gene of HVT and TK Gene of MDV

The whole coding region of the TK gene of HVT (1053 bp) was contained within the 3.2 Kbp HindIII fragment described above (FIG. 3). The sequence of the entire gene and flanking regions is shown in FIG. 5. Similarly the whole of the MDV TK gene is contained within the 3.6 Kbp BamH1 K2 fragment of MDV (FIG. 1). The sequence of MDV TK gene determined so far is shown in FIG. 5. Comparison of the MDV and HVT TK sequences indicates that the two genes have approximately 60% amino acid identity (estimated from 276 amino acid overlap). By contrast, the % amino acid identities between the TK gene of HVT and the TK genes of HSV 1, VZV and EBV are only 30, 27 and 24 respectively (estimated from amino acid overlaps of 320, 332 and 193 respectively). The predicted amino acid sequences of HVT and MDV TK show characteristic ATP and/or CTP binding site motifs described for a number of virus and eukaryotic proteins that are associated with phosphorylation (Gentry, G. A. (1985) Proc. Natl. Acad. Sci. U.S.A. 82, 6815–6819) . These conserved sequences are examples of useful sites for insertion and expression of foreign genes and for producing TK_ deletion mutants.

Example 4

A Antigen Gene of MDV (gP57-65) (gC Homologue)

The A antigen gene is of interest in vaccine development both as an immunogen (it encodes a major glycopolypeptide product) and also because we have identified it as the homologue of HSV gC, a potential non-essential region. The A antigen gene was mapped within the BamH1 B fragment of MDV (Isfort et al 1987), and the nucleotide sequence determined for the GA strain of MDV (Coussens and Velicer, Abstract OP18.51, VII International Congress of Virology, Aug. 9–14, (1987) Edmonton, Canada; J. Virol. 62, 2373–2379). During the random sequencing studies described earlier (Buckmaster et al 1988), we identified an M13 clone (No. 130) which came from the A antigen gene. This clone was then used to identify a 2.3 Kbp EcoR1/PvuII fragment from the RB1B strain of MDV containing the A antigen. This fragment was cloned into a SmaI/EcoR1 cleaved pUC13 vector by standard protocols. One plasmid (pMB419) was sequenced by the M13 dideoxynucleotide method. The sequence of the MDV RB1B A antigen and the predicted amino acid sequence of the protein are presented in FIG. 6. The A antigen regions of MDV and HTV are non-essential genes and they can therefore be used as sites in HDV and HVT into which other genes can be inserted into the virus by homologous recombination. Several lines of evidence support this as outlined below.

1) During our study we isolated and sequenced another RB1B A antigen clone. This had one extra T residue in the string of T's 45 bases 3' to the A antigen ATG codon. This extra T would cause a frameshift which would make it impossible for the gene to encode functional A antigen. As it is probable that this gene was cloned from a replicating MDV, the results suggest that the A antigen is non-essential to the virus.
2) On conducting a similarity search it became clear that the MDV A antigen gene is the homologue of HSV gC and PRV gpIII glycoproteins. Both of these homologous genes are known to be non-essential [for the HSV homologue, see Rosenthal et al (1987) J. Virol. 61, 2438–2447].
3) Strains of MDV lacking A antigen as judged by agar gel diffusion tests [Churchill, A. E. et al (1969) J. gen. Virol.

4, 557–564] or producing low levels using the more sensitive 2D radio-immunoprecipitation [van Zaane, D. et al (1982) Virology 121, 133–146] have been reported.

Furthermore, in view of the fact that the A antigen is a major secreted glycoprotein, it may be a particularly suitable location for the presentation of foreign epitopes within the A antigen as soluble, secreted proteins. This may be achieved by cloning oligonucleotides encoding these epitopes in frame within the A antigen gene.

Strategies for Introducind Genes into HVT and ILTV Vectors

Two possibilities can be envisaged. 1) Insertion into non-essential genes of the vector. 2) Substitution of foreign gene for corresponding gene of the vector. This would be possible only in regions which already have substantial homology as may be the case between some genes of MDV and HVT.

Example 5

Insertion into Non-essential Genes of HVT, ILTV or MDV (a) Insertion at the TK Locus of the Vector 1) HVT, ILTV or MDV may be used as vectors for insertion and expression of avian herpesvirus genes. In particular gB, gD, gH or gC of RB1B MDV may be inserted into ILTV. Also gB and BS-17 of ILTV may be inserted into HVT or MDV. One may use the promoter associated with the inserted gene or use heterologous promoters, including those of a different class of genes (for example the immediate early promoter to optimise expression of gB).
2) ILTV may be used as a general vector for the insertion and expression of genes unrelated to avian herpes viruses and likely to require manipulation of promoters for optimal expression.

The procedure to be used for gene insertion is substantially as described previously for the insertion of hepatitis antigen in HSV [Shih et al, 1984 as above].

MDV and HVT DNA obtained as described above is infectious provided that precautions are taken not to shear the DNA during extraction. Calcium phosphate precipitates of viral DNA prepared as described by Stow and Wilkie [1976) J. gen. Virol. 33, 477] were added to sub-confluent monolayers of CEF. After absorption for 1 h at 37° C., culture medium was added and cultures were incubated for 1 or 2 days until confluent. Monolayers were then trypsinised, replated (1:1 or 1:2 ) in 199 medium (Wellcome) containing 2 to 4% calf serum and incubated at 37° C. until plaques developed, usually after 4 to 5 days. Approximately 200 plaques may be obtained per $\mu$g of HVT DNA and approximately 50 per $\mu$g of MDV DNA.

Restriction enzyme sites than could be used for the insertion of foreign antigens into the TK of HVT strain Fc-126 include: BanII, Bsp1286, DraIII, EcoRI, HincII, HpaI, NheI and NsbII.

Some of these enzymes also have sites in the plasmid vector into which the virus DNA fragments are cloned. Thus in order to linearize the clone DNA without also cutting within the vector, partial digests may be carried out.

None of the above enzymes should cause any disruption to flanking gene, HSV-1 homologues of which are known to play an important role in virus multiplication.

For homologous recombination and isolation of recombinant virus, genes of interest are inserted within non-essential genes such as TK or gC and co-transfected with wild-type viral DNA at molar ratios ranging from 10:1 to 2:1 as described above. Alternatively, intact wild-type virus may be used for co-infection. virus recombination may be detected by 'plaque lifts' which involve transfer of infected cells and released virus which have adhered to the agar overlay to nitrocellulose and hybridization of the denatured DNA released from the cells and virus to suitable probes as described by Villareal, L. et al (1977) Science 196, 183–185. Virus which hybridizes to the probe may be recovered from the monolayer.

A similar procedure may be used to isolate recombinant virus which expressed epitopes of interest. In this instance the nitrocellulose "plaque lifts" are treated with antibody and the presence of bound antibody revealed using a suitable detection system such as labelled protein A or phosphatase conjugated anti-globulin antibody.

The gene of interest with appropriate promoters is first inserted within the cloned TK gene (FIG. 7). The recombinant DNA is then co-transfected with infectious DNA of the vector in chick embryo fibroblasts or chicken kidney cells and $TK^-$ virus may be selected by growth in medium containing acyclovir [Ross, N. (1985) as above] or FMAU [Schat, K. A. et al (1984) Antiviral Research 4, 159–270]. Alternatively, or in addition, plaques are screened for the presence of the gene of interest using 'plaque lifts' on nitrocellulose and hybridization to any relevant labelled probe. Plaques are also screened for expression of the epitopes of interest using monoclonal antibodies or antipeptide antibodies.

The main advantage of this strategy is that the selection procedure increases the chances of obtaining virus recombinants containing the gene of interest. It also offers the opportunity of using different promoters for optimum expression. Thus the use of an immediate early promoter may allow expression in latently infected cells.

(b) Insertion at the gC Locus of the Vector

Since the A antigen (HVT and MDV homologues of HSV gC) is not essential for virus growth in vivo and in vitro (see section on gC above) it is a potentially useful site for the insertion and expression of foreign genes. Moreover, since it is one of the most abundant antigens and is excreted, it may be particularly useful for enhancing the immunogenic properties of foreign proteins. The isolation of virus recombinants at this locus may be achieved by first inserting at least part of the gene of interest in frame within the gC gene and then co-transfecting with infectious viral DNA. Screening of virus plaques with sequence specific probes or wit. specific antibody allows the isolation of recombinants.

Example 6

Substitution of ILTV Genes for Their Homologues in HVT

Substitution may be achieved by co-transfection of cloned ILTV sequences and infectious HVT DNA as described in Example 5. Substitution of genes derived from ILTV for their counterparts in HVT may be effected.

Recombinants expressing ILTV sequences and epitopes may be detected using ILTV-specific monoclonal antibodies or anti-peptide antibodies raised against unique ILTV sequences as described above.

The advantage of this procedure is that it is relatively simple and does not require manipulation of promoters. However, it may be limited to genes which share substantial homology.

Example 7

Strategies for Obtaining $TK^-$ Mutants of TLTV

Deletion mutants. Deletions may be introduced within any suitable part of the gene, for example the domains of the gene that are required for its function as a phosphorylating enzyme such as ATP and CTP binding sites. This may be achieved by restriction enzyme digestion, for example with

Figure 18:
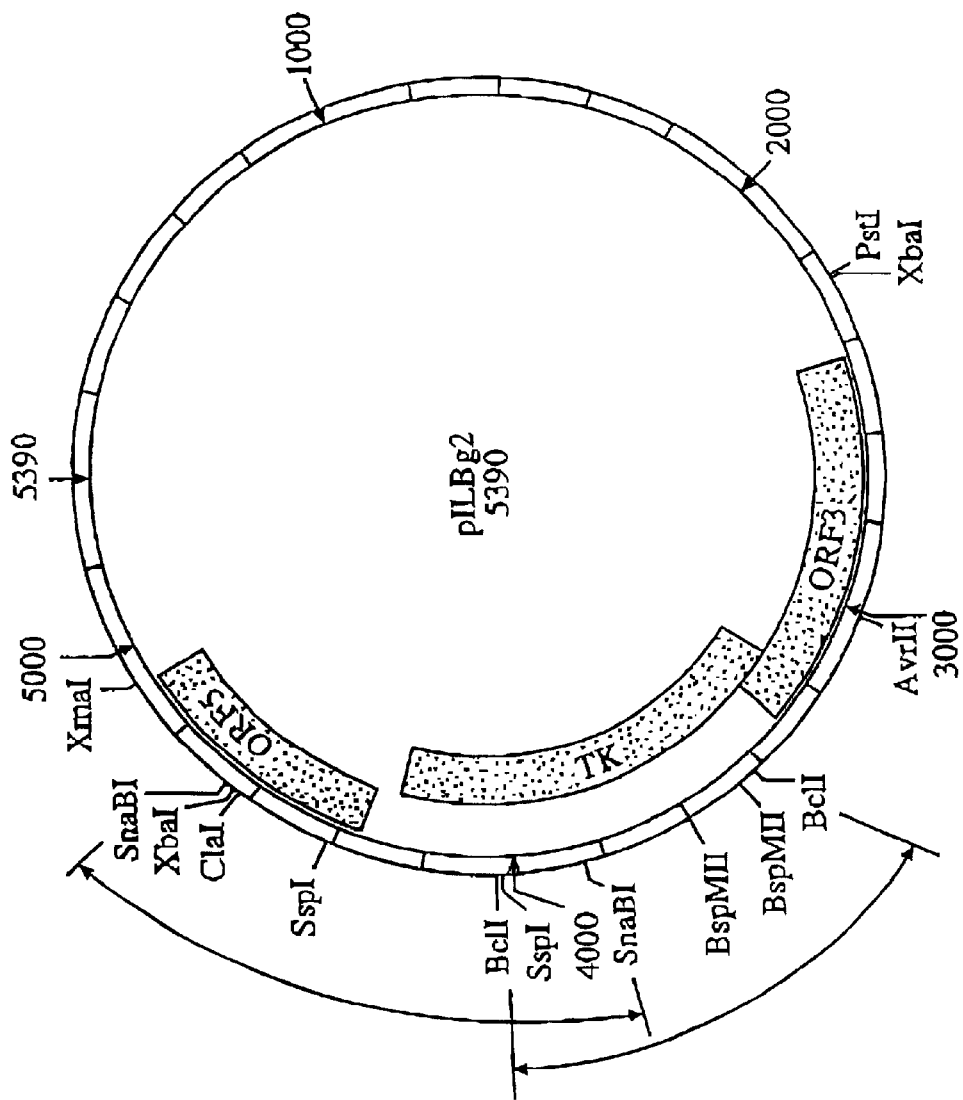
FIG. 18 is a map of plasmid pILBg2, showing restriction sites and the locations of the TK gene and ORFs 3 and 5.

SnaB1 or BclI, and religation off appropriate fragments followed by co-transfection with infectious viral DNA or transfection into virally-infected cells. Reference may be made to FIGS. 7 and 8, and to the map of plasmid pILBg2 (FIG. 18), in choosing restriction enzymes and so on. TK⁻ virus may be selected in the presence of acyclovir [Ross, N. (1985) as above] or FMAU [Schat, K. A. et al (1984) as above]. Plaque-purified clones may then be tested for the absence of the deleted portion of the TK gene by hybridization.

The deletion mutants of ILTV may be used themselves as attenuated viruses for vaccine preparation, or may have sequences for heterologous antigens inserted.

Insertional mutants. A functional β-galactosidase gene under the control of a herpesvirus promoter or any other suitable sequence or a single base is first introduced in a domain of the TK gene which is essential for TK activity. The recombinant DNA is then co-transfected with infectious viral DNA or transfected into virally-infected cells to allow homologous recombination to occur. Selection in the presence of acylovir or FMAU will yield TK-insertional mutants. If a β-galactosidase gene is introduced, mutants can be detected by the production of blue plaques in the presence of X-gal.

The TK gene and surrounding sequences may be subcloned into another suitable vector if necessary.

Example 8
Insertion of MDV RB1B gB Gene into HVT (Not within the scope of the invention, but illustrates an analogous technique).

The HVT TK gene is cloned in the plasmid vector pUC13 to generate a plasmid, which may be termed pTK1B. This plasmid is linearised with, for example, the restriction endonuclease Rsr II which cleaves the plasmid only within the TK gene (nucleotide position 197 in FIG. 5, enzyme recognition sequence CGGACCG). The "sticky" ends thus generated are end repaired by standard techniques (see "Molecular Cloning: a Laboratory Manual", ed. Maniatis T., Fritsch E. F., and Sambrook J. Cold Spring Harbor Laboratory 1982).

The RB1B gB was originally cloned on two plasmids which were termed RB1B-BamH1-I₃ and RB1B-BamH1-K₃. (Note I₃ had lost one BamH1 site during cloning.) To generate a complete gB copy on one plasmid, both plasmids were cleaved with BamH1 and the fragments ligated. However, the complete gB gene was later obtained independently on an EcoRI/SalI fragment. Ross et al, J. gen. Virol (1989) 70, 1789–1804 provides further information regarding the manipulation of viral genes. Recombinants containing tne desired configuration can be identified by restriction enzyme analysis of plasmid DNA's.

The recombinant plasmid is then cleaved with EcoR1, the ends are repaired and the plasmid is cloned into PTK1B prepared as above. The recombinant plasmid is then introduced into cells containing HVT virus (viral DNA) and homologous recombination will introduce the gB gene into the TK gene. HVT viral recombinants can be selected with acyclovir or FMAU or alternatively detected with labelled gB probes.

Example 9
RB1B gC (A Antigen) Gene into HVT

Blunt ended PTK1B is prepared as in Example 8. The RB1B gC is cleaved from the plasmid pMB419 (Example 4) with the restriction endonucleases EcoR1 and HindIII (site within the pUC13 polylinker). The sticky ends generated are again end-repaired by standard protocols. The end-repaired gC fragment is then cloned into the linearized end-repaired pTK1B as in Example 8. (The cloning can be verified by analysis of the resulting clones with restriction enzymes, probing with radio-actively labelled fragments, or DNA sequencing, or any combination of these).

The resulting plasmid pith the RB1b gC gene cloned into the HVT TK gene can then be introduced into the HVT genome by transfecting the plasmid into HVT-infected cells using calcium phosphate precipitation or electro-poration. Homologous recombination, involving crossovers either side of the gC gene, between the HVT virus and the flanking sequences of the HVT TK plasmid will carry the RB1B gC gene into the HVT viral genome. Viral recombinants can be selected for (as they are TK⁻) or identified (eg by probing) as described above.

In analogous ways, the sequence information given above and in the Figures can be used to design cloning strategies for the insertion of these genes and others into the non-essential genes of the ILTV described here or to generate combinations of antigen genes into ILTV.

What is claimed is:

1. A viral vector which comprises a Herpesvirus of Turkeys (HVT) nucleotide sequence consisting essentially of a sequence selected from the group consisting of sequences 887–1078, 1169–1442 and 2187–2423 as shown in FIG. 2, the HVT nucleotide sequence being inserted at a site of the viral vector which is not essential for infectivity and replication, start and stop signals and a promoter allowing expression of the HVT nucleotide sequence.

2. Vector according to claim 1, wherein the vector is a Poxvirus.

3. Vector according to claim 1, wherein the vector is a herpesvirus.

4. Vector according to claim 2, wherein the vector is fowlpoxvirus.

5. Vector according to claim 3, wherein the vector is Marek's Disease Virus of serotype 1, 2 or 3.

6. A plasmid vector which comprises a Herpesvirus of Turkeys (HVT) nucleotide sequence consisting essentially of a sequence selected from the group consisting of sequences 887–1078, 1169–1442 and 2187–2423 as shown in FIG. 2, said plasmid vector being suitable for transfection of Marek's Disease Virus (MDV)- or HVT-susceptible cells.

* * * * *